US009956205B2

(12) United States Patent
Treiber et al.

(10) Patent No.: US 9,956,205 B2
(45) Date of Patent: May 1, 2018

(54) POLYMORPHIC FORMS OF 2-(5-BROMO-4-(4-CYCLOPROPYLNAPHTHALEN-1-YL)-4H-1,2,4-TRIAZOL-3-YLTHIO)ACETIC ACID AND USES THEREOF

(71) Applicant: Ardea Biosciences, Inc., San Diego, CA (US)

(72) Inventors: Laszlo R. Treiber, San Diego, CA (US); Irina Zamansky, Oceanside, CA (US); Jean-Luc Girardet, San Diego, CA (US)

(73) Assignee: Ardea Biosciences, Inc., San Diego, CA (US)

( * ) Notice: Subject to any disclaimer, the term of this patent is extended or adjusted under 35 U.S.C. 154(b) by 0 days. days.

(21) Appl. No.: 15/150,053

(22) Filed: May 9, 2016

(65) Prior Publication Data

US 2016/0250193 A1 Sep. 1, 2016

Related U.S. Application Data

(60) Continuation of application No. 14/577,129, filed on Dec. 19, 2014, now abandoned, which is a continuation of application No. 13/967,255, filed on Aug. 14, 2013, now abandoned, which is a division of application No. 13/339,283, filed on Dec. 28, 2011, now Pat. No. 8,546,436.

(60) Provisional application No. 61/428,660, filed on Dec. 30, 2010.

(51) Int. Cl.
| | |
|---|---|
| A61K 31/4196 | (2006.01) |
| C07D 249/12 | (2006.01) |
| A61K 31/426 | (2006.01) |
| A61K 31/522 | (2006.01) |
| A61K 31/519 | (2006.01) |
| C07D 249/06 | (2006.01) |

(52) U.S. Cl.
CPC ........ *A61K 31/4196* (2013.01); *A61K 31/426* (2013.01); *A61K 31/519* (2013.01); *A61K 31/522* (2013.01); *C07D 249/06* (2013.01); *C07D 249/12* (2013.01)

(58) Field of Classification Search
CPC combination set(s) only.
See application file for complete search history.

(56) References Cited

U.S. PATENT DOCUMENTS

| | | | |
|---|---|---|---|
| 7,435,752 B2 | 10/2008 | Girardet et al. | |
| 8,003,681 B2 | 8/2011 | Girardet et al. | |
| 8,084,483 B2 * | 12/2011 | Quart | C07D 249/12 514/383 |
| 8,173,690 B2 | 5/2012 | Gunic et al. | |
| 8,283,369 B2 | 10/2012 | Quart et al. | |
| 8,357,713 B2 | 1/2013 | Quart et al. | |
| 8,524,754 B2 * | 9/2013 | Zamansky | C07D 249/12 514/383 |
| 8,546,436 B2 | 10/2013 | Galvin et al. | |
| 2008/0176850 A1 | 7/2008 | Girardet et al. | |
| 2010/0056464 A1 | 3/2010 | Gunic et al. | |
| 2012/0164222 A1 | 6/2012 | Quart et al. | |
| 2013/0331403 A1 | 12/2013 | Treiber et al. | |
| 2013/0345271 A1 | 12/2013 | Zamansky et al. | |

FOREIGN PATENT DOCUMENTS

| | | |
|---|---|---|
| JP | 2004123642 A | 4/2004 |
| JP | 2007510758 A | 4/2007 |
| WO | WO-2006026356 A2 | 3/2006 |
| WO | WO-2009070740 A2 | 6/2009 |
| WO | WO-2010028190 A2 | 3/2010 |
| WO | WO-2011085009 A2 | 7/2011 |

OTHER PUBLICATIONS

Aaltonen et al. Solid form screening—a review. European Journal of Pharmaceutics and Biopharmaceutics 71:23-37 (2009).
Brittain. Drugs and the Pharmaceutical Sciences. vol. 95—Polymorphism in Pharmaceutical Solids. (427 pgs.) (1999).
Caira. Crystalline Polymorphism of Organic Compounds. Topics in Current Chemistry. 198:163-208 (Jan. 1998).
Cui et al. A Material Science Perspective of Pharmaceutical Solids. Int'l Journal of Pharmaceuticals. 339:3-18 (2007).
EP11732089 Search Report dated Jun. 6, 2013 (completed May 31, 2013).
Fleischmann et al. Lesinurad (RDEA594), a Novel Uricosuric Agent, in Combination with Febuxostat Shows Significant Additive Urate Lowering Effects in Gout Subjects with 100% Response Achieved for all Combination Dose Regimens. Annual European Congress of Rheumatology Eular, London, Poster # THU0026 (May 25-28, 2011).
Haleblian. Characterization of Habits and Crystalline Modification of Solids and Their Pharmaceutical Applications. Journal of Pharmaceutical Sciences 64(8):1269-1288 (1975).
Kerr et al. Pharmacokinetics and Serum Urate Lowering Effect of RDEA594, a Novel URAT1 Inhibitor, in Gout Patients and Subjects with Varying Degrees of Renal Impairment. (Dallas, Mar. 2-5, 2011).
Kerr et al. Pharmacokinetics, Efficacy and Safety of Lesinurad a Novel URAT1 Inhibitor, in Individuals with Mild to Moderate Renal Impairment. (Chicago. Nov. 5-9, 2011).
Lasko et al. RDEA594, a Novel Uricosuric Agent, Significantly Reduced Serum Urate Levels and Was Well Tolerated in a Phase 2a Pilot Study in Hyperuricemic Gout Patients. (Philadelphia, Oct. 16-21, 2009).
Matsumoto. Yakuzaigaku Manual (Pharmaceutical Science Manual), published from Nanzando.1st Edition, p. 28 and 76 (1989)(w/English Translation).

(Continued)

*Primary Examiner* — Amanda L Aguirre
(74) *Attorney, Agent, or Firm* — Honigman Miller Schwartz & Cohn LLP; Kelly T. Murphy; Jonathan P. O'Brien

(57) ABSTRACT

Crystalline polymorph forms of 2-(5-bromo-4-(4-cyclopropyl naphthalen-1-yl)-4H-1,2,4-triazol-3-ylthio)acetic acid are described. Pharmaceutical compositions and the uses of such compounds, compound forms, and compositions for the treatment of a variety of diseases and conditions are also presented.

12 Claims, 12 Drawing Sheets

(56) References Cited

OTHER PUBLICATIONS

Matsuoka. Advanced Crystallization Technology of Organic Materials—Control of Size, Morphology, Polymorph and Purity, Pharm Tech Japan, 19(6):91(955) (2003) (w/English Translation).
Morisette et al. High-throughput crystallization: polymorphs, slats, co-crystals, and solvates of pharmaceutical solids. Advanced Drug Delivery Reviews 56:275-300 (2004).
Noriaki. Yuukikagoubutsu kessyou sakusei Handbook (Handbook for preparing crystals of organic compounds). p. 10-11, 57-72, 78-81 ( 2008) (w/English Translation).
PCT/US11/020233 International Search Report dated Sep. 9, 2011.
PCT/US11/067657 International Preliminary Report on Patentability dated Jul. 11, 2013.
PCT/US11/067657 International Search Report dated Jul. 18, 2012.
Perez-Ruiz et al. Efficacy and Safety of a Range of Doses of RDEA594, a Novel Uricosuric Agent, as Monotherapy in Gout Patients: Randomized, Double-Blind, Placebo-Controlled, Phase 2 Experience. Annual European Congress of Rheumatology EULAR 2010, Rome (Jun. 16-19, 2010).
Perez-Ruiz et al. Efficacy and Safety of Lesinurad (RDEA594), a Novel URAT1 Inhibitor, in Combination with Allopurinol in Gout Patients with an Inadequate Response to Allopurinol: Results from a Randomized, Blinded, Placebo-Controlled, Phase 2B Extension Study. Annual European Congress of Rheumatology EULAR 2012, Berlin, Poster # FR10370 (Jun. 6-9, 2012).
Perez-Ruiz et al. Efficacy and Safety of Lesinurad (RDEA594), a Novel Uricosuric Agent, Given in Combination with Allopurinol in Allopurinol-Refractory Gout Patients: Randomized, Double Blind, Placebo-Controlled, Phase 2BStudy. EULAR2011 London(May 25-28, 2011).
Shen et al. A RDEA594, a Novel Uricosuric Agent, Shows Significant Additive Activity in Combination with Allopurinol in Gout Patients. ASCPT American Society for Clinical Pharmacology and Therapeutics Annual Meeting, Dallas (Mar. 2-5, 2011).
Singhal et al. Drug polymorphism and Dosage from design: a practical perspective. Advanced Drug Deliver Reviews.56:335-347(2004).
Sundy et al. Efficacy and Safety of Lesinurad (RDEA594), a Novel Uricosuric Agent, Given in Combination with Allopurinol in Allopurinol-Refractory Gout Patients Preliminary Results from Randomized, Blinded, Placebo Controlled, Phase 2B Extension Study. (Chicago, Nov. 9-11, 2011).
Tan et al. Lesinurad (RDEA594), a Investigational Uricosuric Agent for Hyperuricemia and Gout, Blocks OAT4 Transport, Mechanism of Hydrochlorothiazide-Dependent Hyperuricemia. EULAR, London (May 25-28, 2011).
U.S. Appl. No. 13/339,283 Notice of Allowance dated May 24, 2013.
U.S. Appl. No. 13/339,283 Office Action dated May 15, 2013.
U.S. Appl. No. 13/375,607 Notice of Allowance dated May 23, 2013.
U.S. Appl. No. 13/375,607 Office Action dated May 15, 2013.
U.S. Appl. No. 13/954,736 Office Action dated May 13, 2014.
U.S. Appl. No. 13/954,736 Office Action dated Nov. 20, 2013.
U.S. Appl. No. 13/967,255 Office Action dated Jun. 20, 2014.
U.S. Appl. No. 14/577,129 Office Action dated Jul. 6, 2015.
Yang et al. Evaluation of Drug-Drug Interaction Potential Between RDEA594, Allopurinol and Febuxostat in Preclinical Species. (Oct. 16-21, 2009).
Yeh et al. A Novel URAT1 Inhibitor, Shows Significant Additive Urate Lowering Effects in Combination with Febuxostat in Both Healthy Subjects and Gout Patients. (Dallas, Mar. 2-5, 2011).
Yeh et al. Lesinurad (RDEA594), a Novel URAT1 Inhibitor, Shows Additive Serum Urate Lowering Effects in Combination with Xanthine Oxidase Inhibitor Febuxostat. (Apr. 22-25, 2011).
Yeh et al. Mode of Action of RDEA594 as a Uric Acid Lowering Agent in Humans Following Multiple Doses of its Pro-drug, RDEA806. Annual European Congress of Rheumatology EULAR 2008, Paris, Poster # THU0357 (Jun. 11-14, 2008).
Yeh et al. RDEA594, a Novel Uricosuric Agent, Shows Impressive Reductions in Serum Urate Levels as a Monotherapy and Substantial Additive Activity in Combination With Febuxostat in Normal Healthy Volunteers (Rome, Jun. 16-19, 2010).
Yeh et al. RDEA594: A Potent URAT1 Inhibitor Without Affecting Other Important Renal Transporters, OAT1 and OAT3. Annual European Congress of Rheumatology EULAR 2009, Copenhagen, Poster # THU0452 (Jun. 10-13, 2009).
Yeh et al. RDEA594, a Potential Uric Acid Lowering Agent through Inhibition of Uric Acid Reuptake, Shows Better Pharmacokinetics than its Prodrug RDEA806. 2008 ACR-ARHP Annual Scientific Meeting, San Francisco, CA, USA, Poster # 28 (Oct. 24-29, 2008).
Yeh et al. Safety, Pharmacokinetics, and Serum Uric Acid Lowering Effect of RDEA594, a Novel, Uricosuric Agent, in Healthy Volunteers. (Denmark, Jun. 10-13, 2009).
Bavin, Mike, "Polymorphism in Process Development" Chemistry & Industry, 527-529, Aug. 21, 1989.
Bym, Stephen et al., "Pharmaceutical Solids: A Strategic Approach to Regulatory Considerations" Pharmaceutical Research, 12(7): 945-1954, 1995.
European Pharmacopeia, 5th Edition, Fundamental Principles. 787, 2005.
Hancock, Bruno C. et al., "Molecular Mobility of Amorphous Pharmaceutical Solids Below Their Glass Transition Temperatures" Pharmaceutical Research, 12(6): 799-806, 1995.
Opposition to EP265846, Opponent Alfred E. Tiefenbacher (GmbH & Co. KG), Sep. 14, 2017.
Opposition to EP265846, Opponent STADA Arzneimittel AG, Sep. 14, 2017.

* cited by examiner

POLYMORPHIC FORMS OF 2-(5-BROMO-4-(4-CYCLOPROPYLNAPHTHALEN-1-YL)-4H-1,2,4-TRIAZOL-3-YLTHIO)ACETIC ACID AND USES THEREOF

CROSS-REFERENCE

This application is a continuation of U.S. application Ser. No. 14/577,129, filed Dec. 19, 2014, which is a continuation of U.S. application Ser. No. 13/967,255, filed Aug. 14, 2013, now abandoned, which is a divisional of U.S. application Ser. No. 13/339,283, filed Dec. 28, 2011, now issued as U.S. Pat. No. 8,546,436 on Oct. 1, 2013, which claims priority to U.S. Provisional Application No. 61/428,660, filed Dec. 30, 2010, all of which are incorporated herein by reference in their entirety.

FIELD OF THE INVENTION

Described herein are polymorphic forms of 2-(5-bromo-4-(4-cyclopropylnaphthalen-1-yl)-4H-1,2,4-triazol-3-ylthio)acetic acid, which is known to decrease uric acid levels.

BACKGROUND OF THE INVENTION

Gout is associated with elevated levels of uric acid that crystallize and deposit in joints, tendons, and surrounding tissues. Gout is marked by recurrent attacks of red, tender, hot, and/or swollen joints.

SUMMARY OF THE INVENTION

Described herein are crystalline polymorphs of 2-(5-bromo-4-(4-cyclopropylnaphthalen-1-yl)-4H-1,2,4-triazol-3-ylthio)acetic acid:

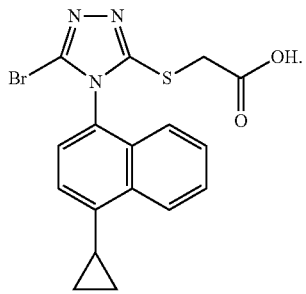

In one aspect described herein are crystalline polymorphs of 2-(5-bromo-4-(4-cyclopropylnaphthalen-1-yl)-4H-1,2,4-triazol-3-ylthio)acetic acid characterized by peaks at 10.32, 18.84 and 20.75 °2θ±0.1°2θ. In further embodiments, such a crystalline polymorph is further characterized by at least two further peaks at 6.80, 21.54, 24.97, 25.53, 27.28 and 27.60 °2θ±0.1°2θ. In yet further embodiments, the crystalline polymorph exhibits an x-ray powder diffraction pattern substantially the same as the x-ray powder diffraction pattern shown in FIG. 1. In yet further embodiments, the crystalline polymorph exhibits an x-ray powder diffraction pattern substantially the same as the x-ray powder diffraction pattern shown in FIG. 2. In a related aspect described herein are crystalline polymorphs of 2-(5-bromo-4-(4-cyclopropylnaphthalen-1-yl)-4H-1,2,4-triazol-3-ylthio)acetic acid, characterized by an endothermic point onset at about 151° C., as determined by differential scanning calorimetry. In a further embodiment, the crystalline polymorph is characterized by a differential scanning calorimetry pattern substantially the same as the differential scanning calorimetry pattern shown in FIG. 3. In another related aspect described herein is the crystalline polymorph form 1 of 2-(5-bromo-4-(4-cyclopropylnaphthalen-1-yl)-4H-1,2,4-triazol-3-ylthio)acetic acid. Also described herein are crystalline polymorphic forms of 2-(5-bromo-4-(4-cyclopropylnaphthalen-1-yl)-4H-1,2,4-triazol-3-ylthio)acetic acid made by a method comprising the step of crystallizing amorphous 2-(5-bromo-4-(4-cyclopropylnaphthalen-1-yl)-4H-1,2,4-triazol-3-ylthio)acetic acid from a mixture of water and acetic acid. In a related aspect described herein, are solid pharmaceutical compositions comprising an effective amount of the crystalline polymorph characterized by the aforementioned diffraction patterns, an effective amount of the crystalline polymorph characterized by the aforementioned differential scanning calorimetry patterns, or an effective amount of the crystalline polymorph form 1, as an active ingredient; and at least one excipient or carrier. Also described herein are methods for treating or preventing hyperuricemia or a disease caused by elevated uric acid levels, comprising administering an effective amount of the crystalline polymorph characterized by the aforementioned diffraction patterns, an effective amount of the crystalline polymorph characterized by the aforementioned differential scanning calorimetry patterns, or an effective amount of the crystalline polymorph form 1. Also described herein are methods for treating or preventing gout, comprising administering an effective amount of the crystalline polymorph characterized by the aforementioned diffraction patterns, an effective amount of the crystalline polymorph characterized by the aforementioned differential scanning calorimetry patterns, or an effective amount of the crystalline polymorph form 1.

In another aspect, described herein are crystalline polymorphs of 2-(5-bromo-4-(4-cyclopropylnaphthalen-1-yl)-4H-1,2,4-triazol-3-ylthio)acetic acid characterized by peaks at 10.46, 18.76, and 19.83 °2θ±0.1°2θ. In further embodiments, such a crystalline polymorph is further characterized by at least one further peak at 18.21 or 23.08 °2θ±0.1°2θ. In yet further embodiments, the crystalline polymorph exhibits an x-ray powder diffraction pattern substantially the same as the x-ray powder diffraction pattern shown in FIG. 5. In yet further embodiments, the crystalline polymorph exhibits an x-ray powder diffraction pattern substantially the same as the x-ray powder diffraction pattern shown in FIG. 6. In a related aspect described herein are crystalline polymorphs of 2-(5-bromo-4-(4-cyclopropyl naphthalen-1-yl)-4H-1,2,4-triazol-3-ylthio)acetic acid, characterized by an endothermic point onset at about 175° C., as determined by differential scanning calorimetry. In a further embodiment, the crystalline polymorph is characterized by a differential scanning calorimetry pattern substantially the same as the differential scanning calorimetry pattern shown in FIG. 8. In another related aspect described herein is the crystalline polymorph form 2 of 2-(5-bromo-4-(4-cyclopropyl naphthalen-1-yl)-4H-1,2,4-triazol-3-ylthio)acetic acid. Also described herein are crystalline polymorphic forms of 2-(5-bromo-4-(4-cyclopropylnaphthalen-1-yl)-4H-1,2,4-triazol-3-ylthio)acetic acid made by a method comprising the step of crystallizing amorphous 2-(5-bromo-4-(4-cyclopropylnaphthalen-1-yl)-4H-1,2,4-triazol-3-ylthio)acetic acid from a mixture of water and ethyl acetate. In a related aspect described herein are solid pharmaceutical compositions comprising an effective amount of the crystalline polymorph characterized by the aforementioned diffraction patterns, an effective amount of the crystalline polymorph characterized by the aforementioned differential scanning calorimetry patterns, or an effective amount of the crystalline polymorph form 2, as an active ingredient; and at least one excipient or carrier. Also described herein are methods for treating or preventing hyperuricemia or a disease caused by elevated uric acid levels, comprising administering an effective amount of the crystalline polymorph characterized by the aforementioned diffraction patterns, an effective amount of the crystalline polymorph characterized by the aforementioned differential scanning calorimetry patterns, or an effective amount of the crystalline polymorph form 2. Also described herein are methods for treating or preventing gout, comprising administering an effective amount of the crystalline polymorph characterized by the aforementioned diffraction patterns, an effective amount of the crystalline polymorph characterized by the aforementioned differential scanning calorimetry patterns, or an effective amount of the crystalline polymorph form 2.

In a further aspect are solid pharmaceutical compositions comprising an effective amount of at least two of the aforementioned crystalline polymorph forms of 2-(5-bromo-4-(4-cyclopropyl naphthalen-1-yl)-4H-1,2,4-triazol-3-yl-thio)acetic acid; and at least one excipient or carrier.

In a further aspect are methods for treating or preventing hyperuricemia or a disease caused by elevated uric acid levels, comprising administering an effective amount of at least two of the aforementioned crystalline polymorph forms of 2-(5-bromo-4-(4-cyclopropylnaphthalen-1-yl)-4H-1,2,4-triazol-3-ylthio)acetic acid; and at least one excipient or carrier.

In a yet further aspect are methods for treating or preventing gout, comprising administering an effective amount of at least two of the aforementioned crystalline polymorph forms of 2-(5-bromo-4-(4-cyclopropylnaphthalen-1-yl)-4H-1,2,4-triazol-3-ylthio)acetic acid; and at least one excipient or carrier.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

While certain embodiments of the present invention have been shown and described herein, it will be obvious to those skilled in the art that such embodiments are provided by way of example only. Numerous variations, changes, and substitutions will occur to those skilled in the art without departing from the invention. It should be understood that various alternatives to the embodiments described herein are, in some circumstances, employed in practicing the invention. It is intended that the following claims define the scope of the invention and that methods and structures within the scope of these claims and their equivalents be covered thereby.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The present invention relates to polymorphic forms of 2-(5-bromo-4-(4-cyclopropyl naphthalen-1-yl)-4H-1,2,4-triazol-3-ylthio)acetic acid, which is known to decrease uric acid levels.

Figure 1:
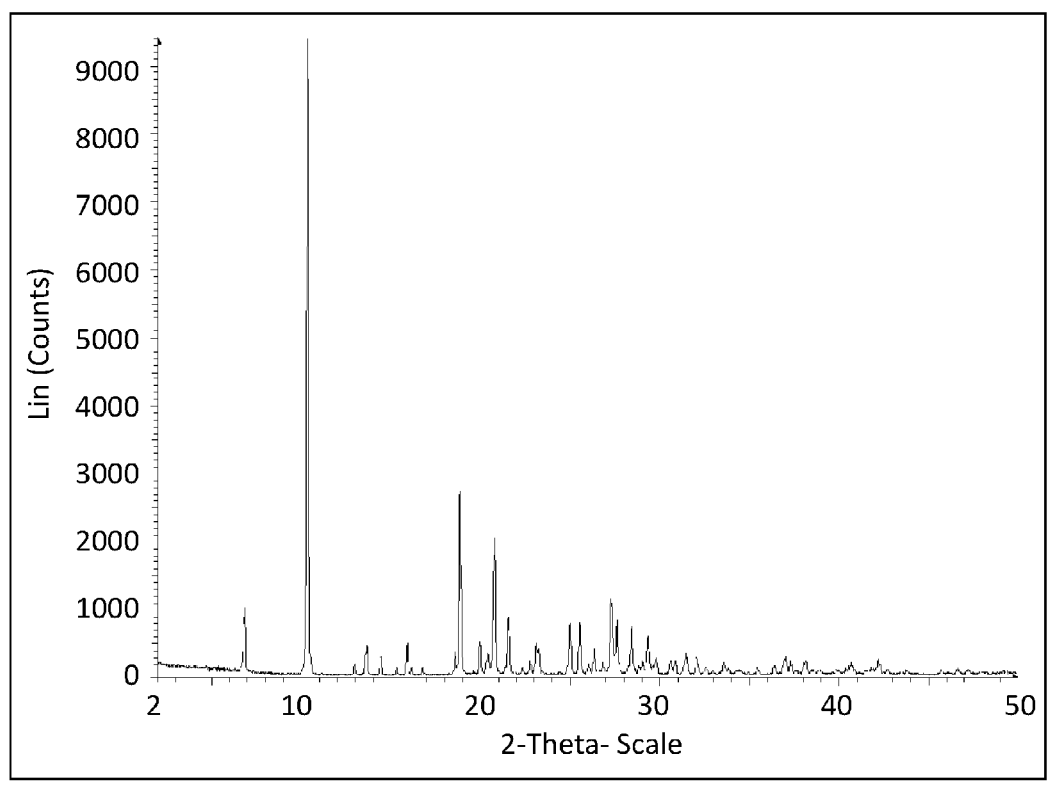
FIG. 1 represents an illustrative X-ray Powder Diffraction Pattern of Polymorph form 1 (Raw Data).
Figure 2:
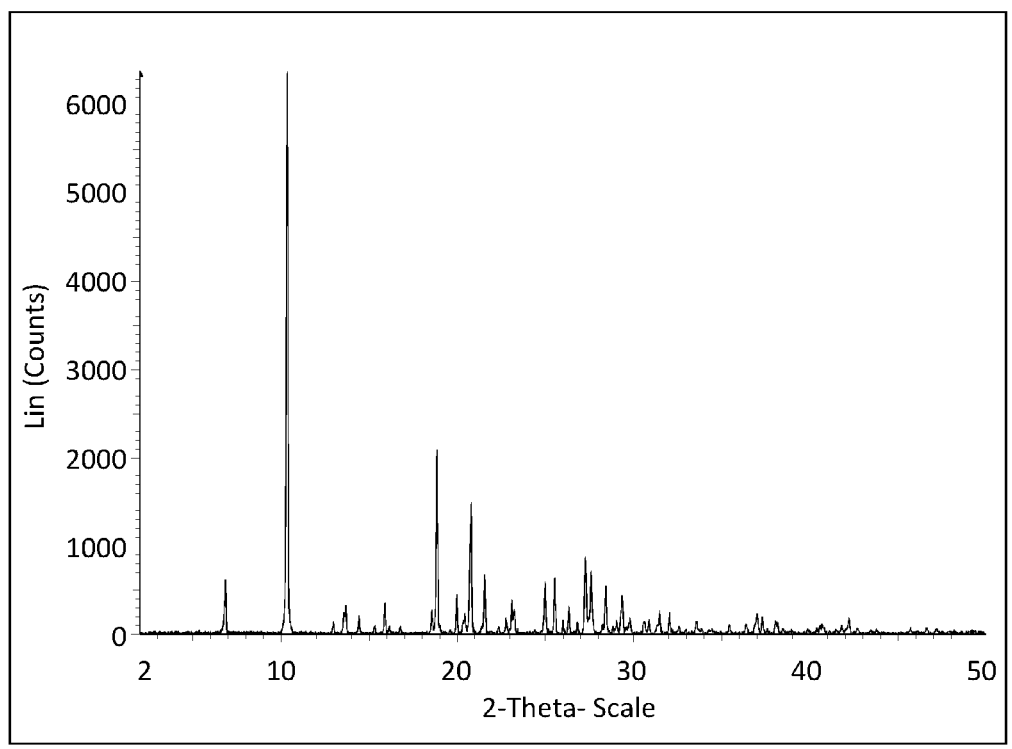
FIG. 2 represents an illustrative X-ray Powder Diffraction Pattern of Polymorph form 1 (Background Subtracted and Kα2 Stripped).
Figure 3:
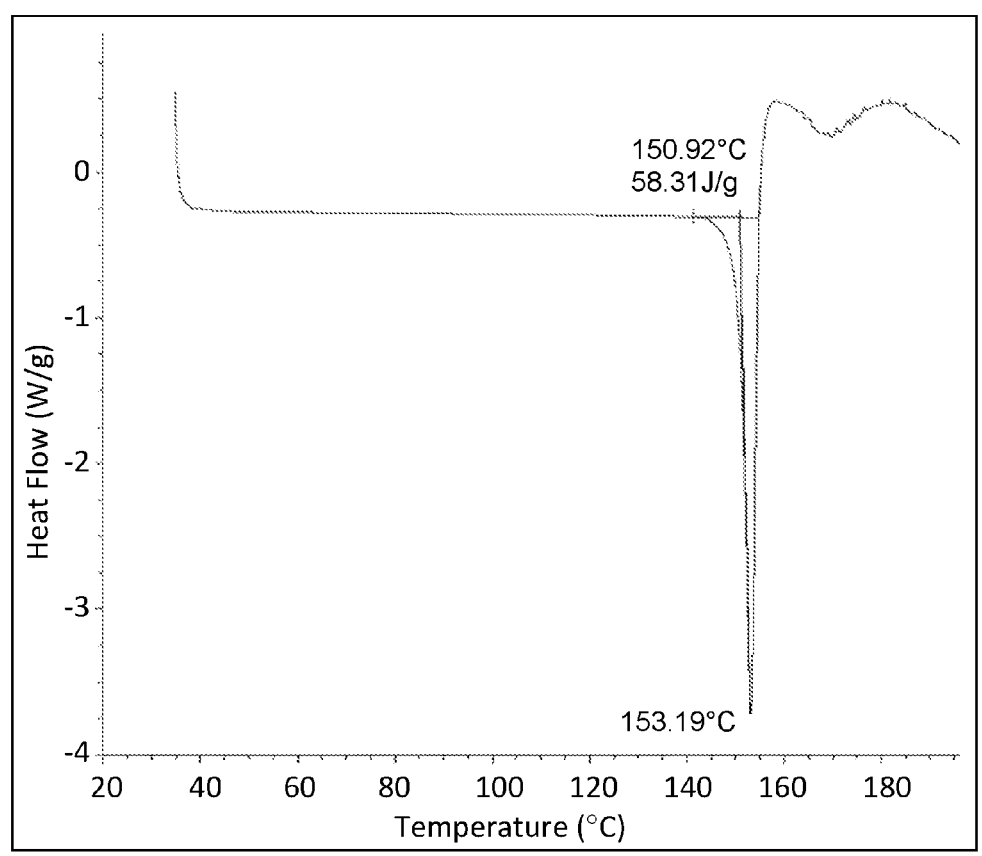
FIG. 3 represents an illustrative Differential Scanning calorimetry pattern of Polymorph form 1.

The term "polymorph form 1" refers to a crystalline form of 2-(5-bromo-4-(4-cyclopropyl naphthalen-1-yl)-4H-1,2,4-triazol-3-ylthio)acetic acid that exhibits an x-ray powder diffraction pattern substantially the same as that shown in FIG. 1, and/or FIG. 2 and/or a differential scanning calorimetry profile substantially the same as that shown in FIG. 3.

Figure 5:
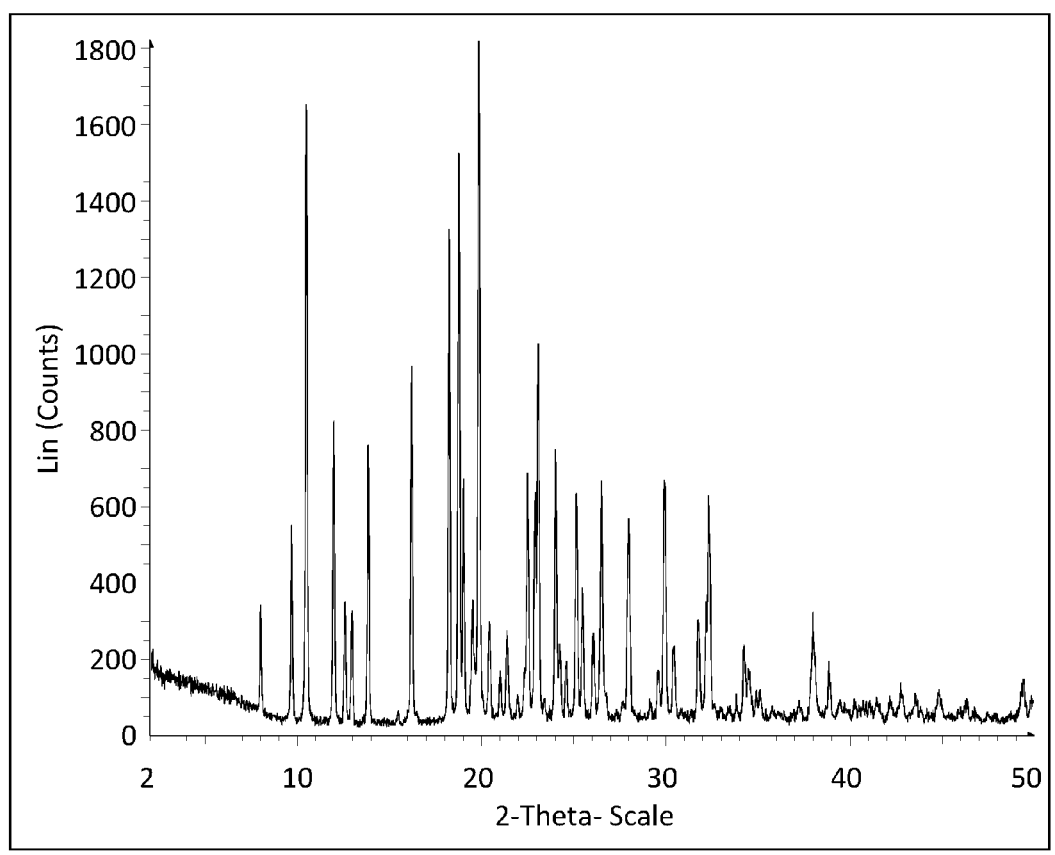
FIG. 5 represents an illustrative X-ray Powder Diffraction Pattern of Polymorph form 2 (Raw Data).
Figure 6:
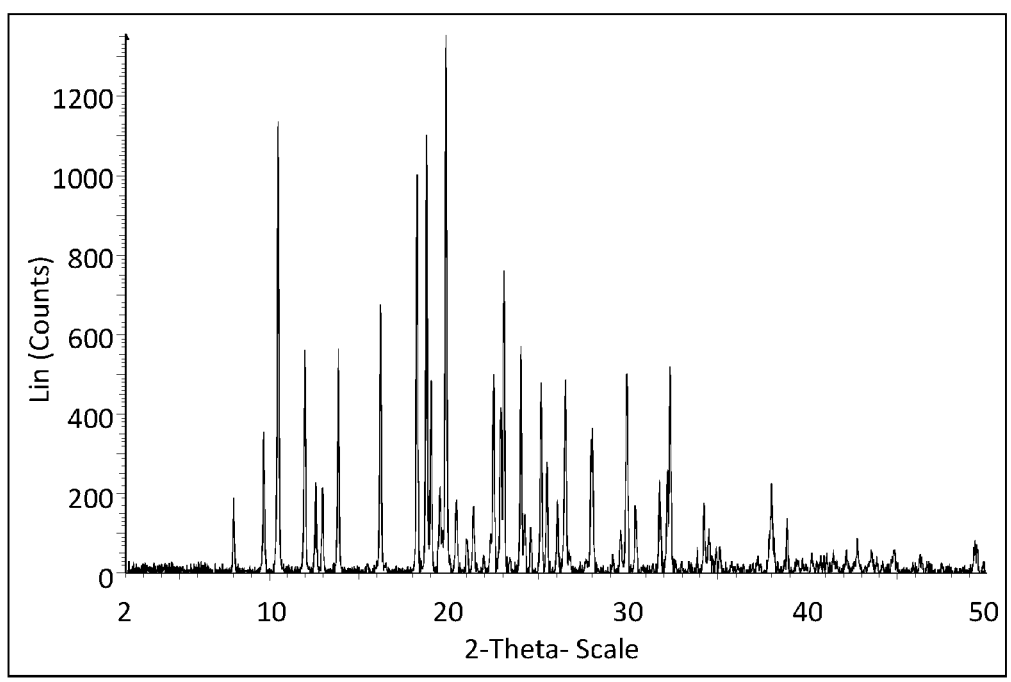
FIG. 6 represents an illustrative X-ray Powder Diffraction Pattern of Polymorph form 2 (Background Subtracted and Kα2 Stripped).
Figure 8:
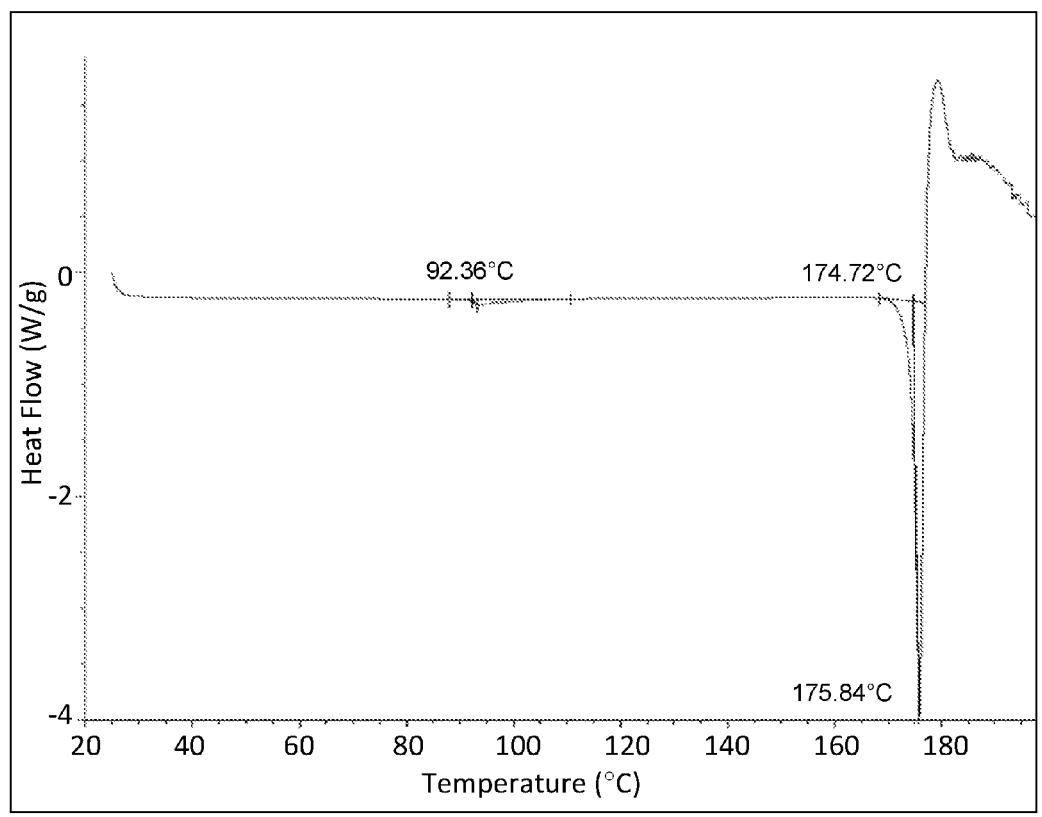
FIG. 8 represents an illustrative Differential Scanning calorimetry pattern of Polymorph form 2.

The term "polymorph form 2" refers to a crystalline form of 2-(5-bromo-4-(4-cyclopropyl naphthalen-1-yl)-4H-1,2,4-triazol-3-ylthio)acetic acid that exhibits an x-ray powder diffraction pattern substantially the same as that shown in FIG. 5, and/or FIG. 6 and/or a differential scanning calorimetry profile substantially the same as that shown in FIG. 8.

The present invention also relates to solid pharmaceutical compositions, comprising, as an active ingredient, an effective amount of 2-(5-bromo-4-(4-cyclopropylnaphthalen-1-yl)-4H-1,2,4-triazol-3-ylthio)acetic acid, as the crystalline polymorph form 1, the crystalline polymorph form 2, or a combination thereof.

The present invention also relates to methods for treating or preventing diseases, comprising administering an effective amount of 2-(5-bromo-4-(4-cyclopropylnaphthalen-1-yl)-4H-1,2,4-triazol-3-ylthio)acetic acid, as the crystalline polymorph form 1, the crystalline polymorph form 2, or a combination thereof.

Also described are processes for the preparation of the crystalline polymorph forms 1 and 2.

2-(5-bromo-4-(4-cyclopropylnaphthalen-1-yl)-4H-1,2,4-triazol-3-ylthio)acetic acid Described herein are polymorph forms of 2-(5-bromo-4-(4-cyclopropylnaphthalen-1-yl)-4H-1,2,4-triazol-3-ylthio)acetic acid which is known to decrease uric acid levels. 2-(5-Bromo-4-(4-cyclopropylnaphthalen-1-yl)-4H-1,2,4-triazol-3-ylthio)acetic acid and related compounds are described in US Patent Application Publications 2008-0176850, US 2009-0197825, US 2010-0056464, US 2010-0056465, US 2010-0069645, and US 2010-0081827.

Polymorph Form 1

In one embodiment, 2-(5-bromo-4-(4-cyclopropylnaphthalen-1-yl)-4H-1,2,4-triazol-3-ylthio)acetate polymorph Form 1 exhibits an x-ray powder diffraction pattern characterized by the diffraction pattern summarized in Table 1A or Table 1B. In some embodiments, provided herein is a polymorph of 2-(5-bromo-4-(4-cyclopropylnaphthalen-1-yl)-4H-1,2,4-triazol-3-ylthio)acetate comprising at least 3 peaks of (±0.1°2θ) of Table 1A or 1B. In certain embodiments, provided herein is a polymorph of 2-(5-bromo-4-(4-cyclopropylnaphthalen-1-yl)-4H-1,2,4-triazol-3-ylthio)acetate comprising at least 4 peaks of (±0.1°2θ) of Table 1A or 1B, at least 5 peaks of (±0.1°2θ) of Table 1A or 1B, at least 6 peaks of (±0.1°2θ) of Table 1A or 1B, at least 8 peaks of (±0.1°2θ) of Table 1A or 1B, at least 10 peaks of (±0.1°2θ) of Table 1A, at least 15 peaks of (±0.1°2θ) of Table 1A, at least 20 peaks of (±0.1°2θ) of Table 1A, at least 25 peaks of (±0.1°2θ) of Table 1A, or at least 30 peaks of (±0.1°2θ) of Table 1A.

TABLE 1A form 1

| °2θ | d space (Å) | Intensity (%) |
|---|---|---|
| 10.32 | 8.562 | 100 |
| 18.84 | 4.706 | 32.7 |
| 20.75 | 4.277 | 23.2 |
| 27.28 | 3.266 | 13.6 |
| 27.60 | 3.229 | 11 |
| 21.54 | 4.123 | 10.4 |
| 25.53 | 3.487 | 9.8 |
| 6.80 | 12.989 | 9.4 |
| 24.97 | 3.563 | 9.1 |
| 28.43 | 3.137 | 8.4 |
| 19.98 | 4.441 | 6.9 |
| 29.35 | 3.040 | 6.7 |
| 15.88 | 5.577 | 5.4 |
| 23.13 | 3.842 | 4.8 |
| 26.34 | 3.381 | 4.8 |
| 18.56 | 4.777 | 4.1 |

TABLE 1B form 1

| °2θ | d space (Å) | Intensity (%) |
|---|---|---|
| 10.32 | 8.562 | 100 |
| 18.84 | 4.706 | 32.7 |
| 20.75 | 4.277 | 23.2 |
| 27.28 | 3.266 | 13.6 |

In one embodiment provided herein, the polymorph form 1 of 2-(5-bromo-4-(4-cyclopropylnaphthalen-1-yl)-4H-1,2,4-triazol-3-ylthio)acetate is characterized by x-ray powder diffraction pattern peaks at 10.32, 18.84, and 20.75 °2θ±0.1°2θ. In further embodiments, the polymorph form 1 is further characterized by at least one peak appearing at 6.80, 21.54, 24.97, 25.53, 27.28 and 27.60 °2θ±0.1°2θ. In further embodiments, the polymorph form 1 is further characterized by at least two peaks appearing at 6.80, 21.54, 24.97, 25.53, 27.28 and 27.60 °2θ±0.1°2θ. In yet still further embodiments, the polymorph exhibits an x-ray powder diffraction pattern substantially the same as the x-ray powder diffraction pattern shown in FIG. 1.

Polymorph Form 2

In one embodiment, 2-(5-bromo-4-(4-cyclopropylnaphthalen-1-yl)-4H-1,2,4-triazol-3-ylthio)acetate polymorph Form 2 exhibits an x-ray powder diffraction pattern characterized by the diffraction pattern summarized in Table 2A or Table 2B. In some embodiments, provided herein is a polymorph of 2-(5-bromo-4-(4-cyclopropylnaphthalen-1-yl)-4H-1,2,4-triazol-3-ylthio)acetate comprising at least 3 peaks of (±0.1°2θ) of Table 2A or 2B. In certain embodiments, provided herein is a polymorph of 2-(5-bromo-4-(4-cyclopropylnaphthalen-1-yl)-4H-1,2,4-triazol-3-ylthio)acetate comprising at least 4 peaks of (±0.1°2θ) of Table 2A or 2B, at least 5 peaks of (±0.1°2θ) of Table 2A or 2B, at least 6 peaks of (±0.1°2θ) of Table 2A or 2B, at least 8 peaks of (±0.1°2θ) of Table 2A or 2B, at least 10 peaks of (±0.1°2θ) of Table 2A, at least 15 peaks of (±0.1°2θ) of Table 2A, at least 20 peaks of (±0.1°2θ) of Table 2A, at least 25 peaks of (±0.1°2θ) of Table 2A, or at least 30 peaks of (±0.1°2θ) of Table 2A.

TABLE 2A form 2 Observed

| °2θ | d space (Å) | Intensity (%) |
|---|---|---|
| 7.97 | 11.086 | 13.8 |
| 9.66 | 9.148 | 26.1 |
| 10.46 | 8.449 | 83.8 |
| 11.96 | 7.394 | 41.3 |
| 12.55 | 7.046 | 16.7 |
| 12.94 | 6.836 | 15.7 |
| 13.82 | 6.402 | 41.6 |
| 16.19 | 5.471 | 49.8 |
| 18.21 | 4.867 | 74.0 |
| 18.76 | 4.727 | 81.4 |
| 19.02 | 4.662 | 35.6 |
| 19.51 | 4.548 | 15.9 |
| 19.83 | 4.474 | 100.0 |
| 20.40 | 4.349 | 13.4 |
| 21.36 | 4.157 | 12.3 |
| 22.50 | 3.948 | 36.7 |
| 22.88 | 3.884 | 30.6 |
| 23.08 | 3.850 | 56.1 |
| 24.01 | 3.704 | 42.1 |
| 25.15 | 3.539 | 35.2 |
| 25.46 | 3.496 | 20.5 |
| 26.06 | 3.417 | 13.4 |
| 26.51 | 3.360 | 35.7 |
| 27.97 | 3.187 | 26.8 |
| 29.93 | 2.983 | 37.0 |
| 30.42 | 2.936 | 12.4 |
| 31.77 | 2.814 | 17.1 |
| 32.35 | 2.765 | 38.2 |
| 34.26 | 2.615 | 12.8 |
| 38.01 | 2.366 | 16.5 |
| 38.88 | 2.314 | 10.0 |

TABLE 2B

| form 2 Representative | | |
|---|---|---|
| °2θ | d space (Å) | Intensity (%) |
| 19.83 | 4.474 | 100.0 |
| 10.46 | 8.449 | 83.8 |
| 18.76 | 4.727 | 81.4 |
| 18.21 | 4.867 | 74.0 |
| 23.08 | 3.850 | 56.1 |

In one embodiment provided herein, the polymorph form 2 of 2-(5-bromo-4-(4-cyclopropylnaphthalen-1-yl)-4H-1,2,4-triazol-3-ylthio)acetate is characterized by x-ray powder diffraction pattern peaks at 10.46, 18.76, and 19.83 °2θ±0.1°2θ. In further embodiments, the polymorph form 2 is further characterized by at least one peak appearing at 18.21, or 23.08 °2θ±0.1°2θ. In further embodiments, the polymorph form 2 is further characterized by two peaks appearing at 18.21, or 23.08 °2θ±0.1°2θ. In yet still further embodiments, the polymorph form 2 exhibits an x-ray powder diffraction pattern substantially the same as the x-ray powder diffraction pattern shown in FIG. 5.

In certain instances, the crystalline polymorphs of 2-(5-bromo-4-(4-cyclopropylnaphthalen-1-yl)-4H-1,2,4-triazol-3-ylthio)acetate were found to exhibit increased stability in comparison to the amorphous solid state form of the carboxylic acid. In some instances, improved stability of the crystalline polymorphs of 2-(5-bromo-4-(4-cyclopropylnaphthalen-1-yl)-4H-1,2,4-triazol-3-ylthio)acetate provides for the preparation of pharmaceutical dosage forms displaying reduced variability in the dosage present in a given dosage form, reduction in the presence of impurities in the final pharmaceutical product, and an improved shelf life of formulated dosage forms when compared to the pharmaceutical dosage form prepared with the amorphous solid state form of the carboxylic acid. In some embodiments, a polymorph described herein (e.g., Form 1 or Form 2) demonstrates no degradation (e.g., less than 0.01%, less than 0.1%, less than 0.5% by wt.) for at least 3 months under accelerated conditions (e.g., 40° C.-75% RH), for at least 4 months under accelerated conditions (e.g., 40° C.-75% RH), for at least 5 months under accelerated conditions (e.g., 40° C.-75% RH), for at least 6 months under accelerated conditions (e.g., 40° C.-75% RH), for at least 9 months under accelerated conditions (e.g., 40° C.-75% RH), for at least 12 months under accelerated conditions (e.g., 40° C.-75% RH), and/or (ii) for at least 12 months under long-term conditions (e.g., 25° C.-60% RH), for at least 18 months under long-term conditions (e.g., 25° C.-60% RH), for at least 24 months under long-term conditions (e.g., 25° C.-60% RH).

Figure 12:
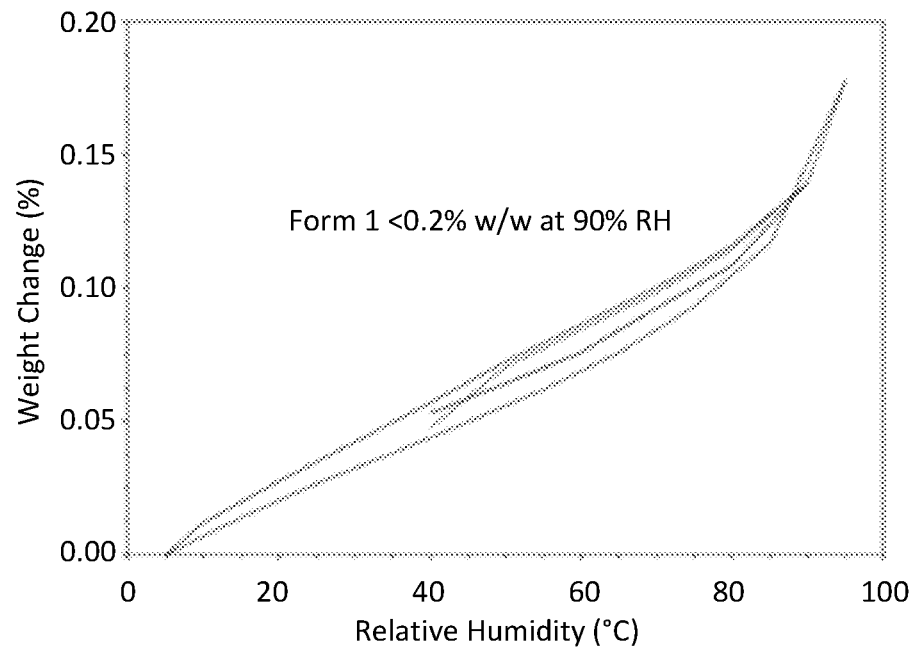
FIG. 12 represents an illustrative Gravimetric Vapor Sorption study of Polymorph form 1 and 2.
Figure 12:
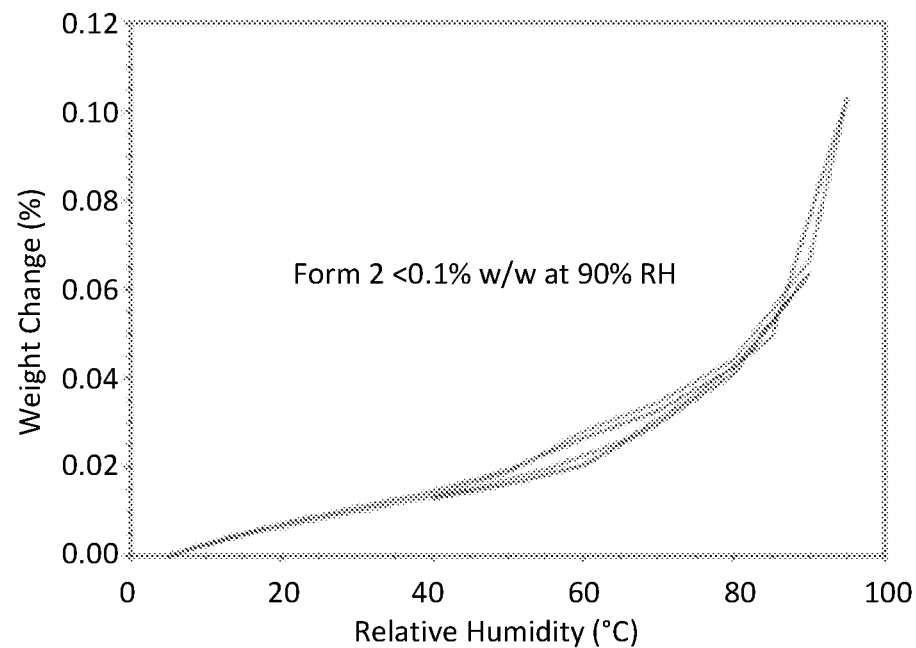

Additionally, in certain instances, the crystalline polymorphs of 2-(5-bromo-4-(4-cyclopropylnaphthalen-1-yl)-4H-1,2,4-triazol-3-ylthio)acetate were found to exhibit decreased hygroscopicity compared to other solid state forms as determined by gravimetric vapor sorption (GVS) studies. FIG. 12 illustrates a GVS study of form 1 and form 2. Form 1 was found to adsorb <0.2% w/w at high humidity and Form 2 was found to adsorb <0.1% w/w at high humidity. This property of decreased hygroscopicity greatly aids in the preparation of solid pharmaceutical dosage forms.

Admixture with Amorphous Solid State Forms

In certain embodiments, any of the polymorphs described herein (e.g., Form 1) optionally comprises (or is intermixed or in combination with) a certain amount of amorphous 2-(5-bromo-4-(4-cyclopropylnaphthalen-1-yl)-4H-1,2,4-triazol-3-ylthio)acetate. In some embodiments, the amorphous component of the polymorph (e.g., Form 1) or polymorph combination comprises less than 50 wt. % of the polymorph or polymorph combination, less than 25 wt. % of the polymorph or polymorph combination, less than 15 wt. % of the polymorph or polymorph combination, less than 10 wt. % of the polymorph or polymorph combination, or less than 5 wt. % of the polymorph or polymorph combination.

Particle Size

In certain embodiments, provided herein is a 2-(5-bromo-4-(4-cyclopropylnaphthalen-1-yl)-4H-1,2,4-triazol-3-ylthio)acetate polymorph particle (e.g., crystalline, or comprising a crystalline component). In some embodiments, provided herein is a 2-(5-bromo-4-(4-cyclopropylnaphthalen-1-yl)-4H-1,2,4-triazol-3-ylthio)acetate polymorph (e.g., crystalline, or comprising a crystalline component) having a particle size of about 5-50 microns. In some embodiments, the average particle size is at least 10 microns, 15-50 microns, 15-35 microns, 35-45 microns, 35-40 microns, about 40 microns, or the like. In some embodiments, particles of 2-(5-bromo-4-(4-cyclopropylnaphthalen-1-yl)-4H-1,2,4-triazol-3-ylthio)acetate (e.g., crystalline, or comprising a crystalline component, such as a polymorph of Form 1) having an average diameter of greater than 5 or 10 microns have improved stability parameters compared to smaller diameters.

Uric acid is the result of the oxidation of xanthine. Disorders of uric acid metabolism include, but are not limited to, polycythemia, myeloid metaplasia, gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis or sarcoidosis.

Definitions

The term "subject", as used herein in reference to individuals suffering from a disorder, and the like, encompasses mammals and non-mammals. In one embodiment of the methods and compositions provided herein, the mammal is a human.

The terms "effective amount", "therapeutically effective amount" or "pharmaceutically effective amount" as used herein, refer to an amount of at least one agent or compound being administered that is sufficient to treat or prevent the particular disease or condition. The result is the reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case is determined using techniques such as a dose escalation study.

The term "substantially the same as" as used herein, refers to a powder x-ray diffraction pattern or differential scanning calorimetry pattern that is non-identical to those depicted herein, but that falls within the limits of experimental error, when considered by one of ordinary skill in the art.

Modulating URAT-1 Activity

Also described herein are methods of modulating URAT-1 activity by contacting URAT-1 with an amount of a polymorphic form of 2-(5-bromo-4-(4-cyclopropylnaphthalen-1-yl)-4H-1,2,4-triazol-3-ylthio)acetic acid, as described herein, sufficient to modulate the activity of URAT-1. The term "modulate" refers to either inhibiting or activating URAT-1 activity. In some embodiments are provided methods of inhibiting DRAT-1 activity by contacting URAT-1 with an amount of a polymorphic form of 2-(5-bromo-4-(4-cyclopropylnaphthalen-1-yl)-4H-1,2,4-triazol-3-ylthio)acetic acid, as described herein, sufficient to inhibit the activity of DRAT-1. In some embodiments are provided methods of inhibiting DRAT-1 activity in a solution by contacting said solution with an amount of a polymorphic form of 2-(5-bromo-4-(4-cyclopropylnaphthalen-1-yl)-4H-1,2,4-triazol-3-ylthio)acetic acid, as described herein sufficient to inhibit the activity of URAT-1 in said solution. In some embodiments are provided methods of inhibiting URAT-1 activity in a cell by contacting said cell with an amount of a polymorphic form of 2-(5-bromo-4-(4-cyclopropylnaphthalen-1-yl)-4H-1,2,4-triazol-3-ylthio)acetic acid, as described herein, sufficient to inhibit the activity of URAT-1 in said cell. In some embodiments are provided methods of inhibiting URAT-1 activity in a tissue by contacting said tissue with an amount of a polymorphic form of 2-(5-bromo-4-(4-cyclopropylnaphthalen-1-yl)-4H-1,2,4-triazol-3-ylthio)acetic acid, as described herein, sufficient to inhibit the activity of URAT-1 in said tissue. In some embodiments are provided methods of inhibiting URAT-1 activity in blood by contacting the blood with an amount of a polymorphic form of 2-(5-bromo-4-(4-cyclopropylnaphthalen-1-yl)-4H-1,2,4-triazol-3-ylthio)acetic acid, as described herein, sufficient to inhibit the activity of URAT-1 in blood. In some embodiments are provided methods of inhibiting URAT-1 activity in plasma by contacting the plasma with an amount of a polymorphic form of 2-(5-bromo-4-(4-cyclopropylnaphthalen-1-yl)-4H-1,2,4-triazol-3-ylthio)acetic acid, as described herein, sufficient to inhibit the activity of DRAT-1 in plasma. In some embodiments are provided methods of inhibiting URAT-1 activity in an animal by contacting said animal with an amount of a polymorphic form of 2-(5-bromo-4-(4-cyclopropylnaphthalen-1-yl)-4H-1,2,4-triazol-3-ylthio)acetic acid, as described herein sufficient to inhibit the activity of URAT-1 in said animal. In some embodiments are provided methods of inhibiting URAT-1 activity in a mammal by contacting said mammal with an amount of a polymorphic form of 2-(5-bromo-4-(4-cyclopropylnaphthalen-1-yl)-4H-1,2,4-triazol-3-ylthio)acetic acid, as described herein sufficient to inhibit the activity of URAT-1 in said mammal. In some embodiments are provided methods of inhibiting URAT-1 activity in a human by contacting said human with an amount of a polymorphic form of 2-(5-bromo-4-(4-cyclopropylnaphthalen-1-yl)-4H-1,2,4-triazol-3-ylthio)acetic acid, as described herein, sufficient to inhibit the activity of URAT-1 in said human.

Pharmaceutical Compositions

Described herein are pharmaceutical compositions comprising an effective amount of a polymorphic form of 2-(5-bromo-4-(4-cyclopropylnaphthalen-1-yl)-4H-1,2,4-triazol-3-ylthio)acetic acid, as described herein. In some embodiments, the pharmaceutical compositions comprise an effective amount of a polymorphic form of 2-(5-bromo-4-(4-cyclopropylnaphthalen-1-yl)-4H-1,2,4-triazol-3-ylthio) acetic acid, as described herein, and at least one pharmaceutically acceptable carrier. In some embodiments, the pharmaceutical compositions comprise an effective amount of polymorphic form 1, as described herein, and at least one pharmaceutically acceptable carrier. In some embodiments, the pharmaceutical compositions comprise an effective amount of polymorphic form 2, as described herein, and at least one pharmaceutically acceptable carrier. In some embodiments, the pharmaceutical compositions comprise an effective amount of a combination of polymorphic form 1 and form 2, as described herein, and at least one pharmaceutically acceptable carrier. In some embodiments the pharmaceutical compositions are for the treatment of disorders. In some embodiments the pharmaceutical compositions are for the treatment of disorders in a mammal. In some embodiments the pharmaceutical compositions are for the treatment of disorders in a human. In some embodiments the pharmaceutical compositions are for the treatment or prophylaxis of disorders of uric acid metabolism. In some embodiments the pharmaceutical compositions are for the treatment or prophylaxis of hyperuricemia. In some embodiments the pharmaceutical compositions are for the treatment or prophylaxis of gout.

Modes of Administration, Formulations and Dosage Forms

Described herein are pharmaceutical compositions comprising a polymorphic form of 2-(5-bromo-4-(4-cyclopropylnaphthalen-1-yl)-4H-1,2,4-triazol-3-ylthio)acetic acid, as described herein. The compound, compound forms and compositions described herein are administered either alone, or in combination with, pharmaceutically acceptable carriers, excipients, or diluents in a pharmaceutical composition, according to standard pharmaceutical practice. Administration is effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route depends upon, for example, the condition and disorder of the recipient. Those of skill in the art will be familiar with administration techniques that can be employed with the compounds, compound forms, compositions and methods described herein. By way of example only, the compounds, compound forms and compositions described herein are, in some embodiments, administered locally to the area in need of treatment, by for example, local infusion during surgery, topical application such as creams or ointments, injection, catheter, or implant, said implant made for example, out of a porous, non-porous, or gelatinous material, including membranes, such as sialastic membranes, or fibers. The administration is, in some embodiments, by direct injection at the site of a diseased tissue or organ.

The pharmaceutical compositions described herein are, for example, in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition is, in some embodiments, in unit dosage forms suitable for single administration of precise dosages. Pharmaceutical compositions include a compound or compound form as described herein as an active ingredient, and a conventional pharmaceutical carrier or excipient. In some embodiments these compositions include other or additional medicinal or pharmaceutical agents, carriers, adjuvants, etc.

Pharmaceutical compositions are conveniently presented in unit dosage form.

In some embodiments, they are prepared with a specific amount of active compound by any of the methods well known or apparent to those skilled in the pharmaceutical arts.

Doses

The amount of pharmaceutical compositions administered will firstly be dependent on the mammal being treated. In the instances where pharmaceutical compositions are administered to a human subject, the daily dosage will normally be determined by the prescribing physician with the dosage generally varying according to the age, sex, diet, weight, general health and response of the individual patient, the severity of the patient's symptoms, the precise indication or condition being treated, the severity of the indication or condition being treated, time of administration, route of administration, the disposition of the composition, rate of excretion, drug combination, and the discretion of the prescribing physician. Also, the route of administration vary depending on the condition and its severity. The pharmaceutical composition is, in some embodiments, in unit dosage form. In such form, the preparation is subdivided into unit doses containing appropriate quantities of the active component, e.g., an effective amount to achieve the desired purpose. Determination of the proper dosage for a particular situation is within the skill of the art. For convenience, in some embodiments, the total daily dosage is divided and administered in portions during the day if desired. The amount and frequency of administration will be regulated according to the judgment of the attending clinician physician considering such factors as described above. Thus the amount of pharmaceutical composition to be administered is variable depending upon the circumstances. Administration occurs in an amount of between about 0.001 mg/kg of body weight to about 100 mg/kg of body weight per day (administered in single or divided doses), or at least about 0.1 mg/kg of body weight per day. A particular therapeutic dosage includes, in some embodiments, from about 0.01 mg to about 7000 mg of compound, or, from about 0.05 mg to about 2500 mg. The quantity of active compound in a unit dose of preparation is, in some embodiments, varied or adjusted from about 0.1 mg to 1000 mg, from about 1 mg to 300 mg, or 10 mg to 200 mg, according to the particular application. In some instances the particular therapeutic dosage is about 200 mg, about 300 mg, about 400 mg, about 500 mg, about 600 mg, about 700 mg or about 800 mg. In some instances, dosage levels below the lower limit of the aforesaid range are more than adequate, while in other cases still larger doses are employed without causing any harmful side effect, e.g. by dividing such larger doses into several small doses for administration throughout the day. In combinational applications in which the compound is not the sole therapy, it is possible to administer lesser amounts of compound and still have therapeutic or prophylactic effect.

Combination Therapies

The compounds and compound forms described herein are administered as a sole therapy or in combination with another therapy or therapies.

By way of example only, if one of the side effects experienced by a patient upon receiving a compound or compound form as described herein is hypertension, then it may be appropriate to administer an anti-hypertensive agent in combination with the compound. Or, by way of example only, the therapeutic effectiveness of a compound or compound form as described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit experienced by a patient may be increased by administering a compound or compound form as described herein with another therapeutic agent (which also includes a therapeutic regimen) that also has therapeutic benefit. Regardless of the disease, disorder or condition being treated, the overall benefit experienced by the patient may simply be additive of the two therapeutic agents or the patient may experience a synergistic benefit.

In the instances where the compounds or compound forms as described herein are administered with other therapeutic agents, they need not be administered in the same pharmaceutical composition as other therapeutic agents, and may, because of different physical and chemical characteristics, be administered by a different route. For example, the compound or compound form as described herein may be administered orally to generate and maintain good blood levels thereof, while the other therapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The compounds, compound forms and compositions described herein (and where appropriate other chemotherapeutic agent) may be administered concurrently (e.g., simultaneously, essentially simultaneously or within the same treatment protocol) sequentially or separately, depending upon the nature of the disease, the condition of the patient, and the actual choice of other chemotherapeutic agent to be administered. For combinational applications and uses, the compounds, compound forms and compositions described herein and the chemotherapeutic agent need not be administered simultaneously or essentially simultaneously. Thus, the compounds, compound forms and compositions as described herein may be administered first followed by the administration of the chemotherapeutic agent; or the chemotherapeutic agent may be administered first followed by the administration of the compounds, compound forms and compositions as described herein. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the chemotherapeutic agent may be administered first, especially if it is a cytotoxic agent, and then the treatment continued with the administration of the compounds, compound forms and compositions as described herein followed, where determined advantageous, by the administration of the chemotherapeutic agent, and so on until the treatment protocol is complete. Thus, in accordance with experience and knowledge, the practicing physician can modify each administration protocol for treatment according to the individual patient's needs, as the treatment proceeds. The attending clinician, in judging whether treatment is effective at the dosage administered, will consider the general well-being of the patient as well as more definite signs such as relief of disease-related symptoms. Relief of disease-related symptoms such as pain, and improvement in overall condition can also be used to help judge effectiveness of treatment.

Specific, non-limiting examples of possible combination therapies include use of the compounds, compound forms and compositions described herein with Febuxostat, Allopurinol, Probenecid, Sulfinpyrazone, Losartan, Fenofibrate, Benzbromarone or PNP-inhibitors (such as, but not limited to Forodesine, BCX-1777 or BCX-4208). This list should not be construed to be closed, but should instead serve as an illustrative example common to the relevant therapeutic area at present. Moreover, combination regimens may include a variety of routes of administration, including but not limited to oral, intravenous, intraocular, subcutaneous, dermal, and inhaled topical.

Diseases

Described herein are methods of treating a disease or disorder in an individual suffering from the disease or disorder comprising administering to said individual an effective amount of a polymorph form as described herein of 2-(5-bromo-4-(4-cyclopropylnaphthalen-1-yl)-4H-1,2,4-triazol-3-ylthio)acetic acid.

Also described herein are methods of preventing a disease or disorder in an individual comprising administering to said individual an effective amount of a polymorph form as described herein of 2-(5-bromo-4-(4-cyclopropylnaphthalen-1-yl)-4H-1,2,4-triazol-3-ylthio)acetic acid.

The invention extends to the use of the compounds, compound forms and compositions described herein, in the manufacture of a medicament for treating or preventing a disease or disorder.

In some embodiments, the disease or disorder is hyperuricemia. In certain instances, hyperuricemia is characterized by higher than normal blood levels of uric acid, sustained over long periods of time. In certain instances, increased blood urate levels may be due to enhanced uric acid production (~10-20%) and/or reduced renal excretion (~80-90%) of uric acid. In certain instances, causes of hyperuricemia may include obesity/weight gain, excessive alcohol use, excessive dietary purine intake (foods such as shellfish, fish roe, scallops, peas lentils, beans and red meat, particularly offal-brains, kidneys, tripe, liver), certain medications, including low-dose aspirin, diuretics, niacin, cyclosporine, pyrazinamide, ethambutol, some high blood pressure drugs and some cancer chemotherapeutics, immunosuppressive and cytotoxic agents, specific disease states, particularly those associated with a high cell turnover rate (such as malignancy, leukemia, lymphoma or psoriasis), and also including high blood pressure, hemoglobin diseases, hemolytic anemia, sickle cell anemia, various nephropathies, myeloproliferative and lymphoproliferative diseases, hyperparathyroidism, renal disease, conditions associated with insulin resistance and diabetes mellitus, and in transplant recipients, and possibly heart disease, inherited enzyme defects, abnormal kidney function (e.g. increased ATP turn over, reduced glomerular urate filtration) and exposure to lead (plumbism or "saturnine gout").

In certain instances, hyperuricemia may be asymptomatic, though is associated with the following conditions: gout, gouty arthritis, uric acid stones in the urinary tract (urolithiasis), deposits of uric acid in the soft tissue (tophi), deposits of uric acid in the kidneys (uric acid nephropathy), and impaired kidney function, possibly leading to chronic and acute renal failure.

In further or additional embodiments, the disease or disorder is gout, which is a condition that results from uric acid crystals depositing in tissues of the body. It is often related to an inherited abnormality in the body's ability to process uric acid, but may also be exacerbated by a purine rich diet. Defective uric acid processing may lead to elevated levels of uric acid in the blood causing recurring attacks of joint inflammation (arthritis), uric acid deposits in and around the joints, tophaceous gout, the formation of tophi, decreased kidney function, and kidney stones. Approximately 3-5 million people in the United States suffer from attacks of gout with attacks more prevalent in men than in women. In certain instances, gout is one of the most common forms of arthritis, accounting for approximately 5% of all arthritis cases. In certain instances, kidney failure and urolithiasis occur in 10-18% of individuals with gout and are common sources of morbidity and mortality from the disease.

Gout is associated with hyperuricemia. In certain instances, individuals suffering from gout excrete approximately 40% less uric acid than non-gouty individuals for any given plasma urate concentration. In certain instances, urate levels increase until the saturation point is reached. In certain instances, precipitation of urate crystals occurs when the saturation point is reached. In certain instances, these hardened, crystallized deposits (tophi) form in the joints and skin, causing joint inflammation (arthritis). In certain instances, deposits are be made in the joint fluid (synovial fluid) and/or joint lining (synovial lining). Common areas for these deposits are the large toe, feet, ankles and hands (less common areas include the ears and eyes). In certain instances, the skin around an affected joint becomes red and shiny with the affected area being tender and painful to touch. In certain instances, gout attacks increase in frequency. In certain instances, untreated acute gout attacks lead to permanent joint damage and disability. In certain instances, tissue deposition of urate leads to: acute inflammatory arthritis, chronic arthritis, deposition of urate crystals in renal parenchyma and urolithiasis. In certain instances, the incidence of gouty arthritis increases 5 fold in individuals with serum urate levels of 7 to 8.9 mg/dL and up to 50 fold in individuals with levels >9 mg/dL (530 µmol/L). In certain instances, individuals with gout develop renal insufficiency and end stage renal disease (i.e., "gouty nephropathy"). In certain instances, gouty nephropathy is characterized by a chronic interstitial nephropathy, which is promoted by medullary deposition of monosodium urate.

In certain instances, gout includes painful attacks of acute, monarticular, inflammatory arthritis, deposition of urate crystals in joints, deposition of urate crystals in renal parenchyma, urolithiasis (formation of calculus in the urinary tract), and nephrolithiasis (formation of kidney stones). In certain instances, secondary gout occurs in individuals with cancer, particularly leukemia, and those with other blood diseases (e.g. polycythemia, myeloid metaplasia, etc).

In certain instances, attacks of gout develop very quickly, frequently the first attack occurring at night. In certain instances, symptoms include sudden, severe joint pain and extreme tenderness in the joint area, joint swelling and shiny red or purple skin around the joint. In certain instances, the attacks are infrequent lasting 5-10 days, with no symptoms between episodes. In certain instances, attacks become more frequent and last longer, especially if the disease is not controlled. In certain instances, episodes damage the affected joint(s) resulting in stiffness, swelling, limited motion and/or persistent mild to moderate pain.

Plumbism or "saturnine gout," is a lead-induced hyperuricemia that results from lead inhibition of tubular urate transport causing decreased renal excretion of uric acid. In certain instances, more than 50% of individuals suffering from lead nephropathy suffer from gout. In certain instances, acute attacks of saturnine gout occur in the knee more frequently than the big toe. In certain instances, renal disease is more frequent and more severe in saturnine gout than in primary gout. In certain instances, treatment consists of excluding the individual from further exposure to lead, the use of chelating agents to remove lead, and control of acute gouty arthritis and hyperuricemia. In certain instances, saturnine gout is characterized by less frequent attacks than primary gout. In certain instances, lead-associated gout occurs in pre-menopausal women, an uncommon occurrence in non lead-associated gout.

In certain instances, Lesch-Nyhan syndrome (LNS or Nyhan's syndrome) affects about one in 100,000 live births. In certain instances, LNS is caused by a genetic deficiency of the enzyme hypoxanthine-guanine phosphoribosyltransferase (HGPRT). In certain instances, LNS is an X-linked recessive disease. In certain instances, LNS is present at birth in baby boys. In certain instances, the disease leads to severe gout, poor muscle control, and moderate mental retardation, which appear in the first year of life. In certain instances, the disease also results in self-mutilating behaviors (e.g., lip and finger biting, head banging) beginning in the second year of life. In certain instances, the disease also results in gout-like swelling in the joints and severe kidney problems. In certain instances, the disease leads neurological symptoms include facial grimacing, involuntary writhing, and repetitive movements of the arms and legs similar to those seen in Huntington's disease. The prognosis for individuals with LNS is poor. In certain instances, the life expectancy of an untreated individual with LNS is less than about 5 years. In certain instances, the life expectancy of a treated individual with LNS is greater than about 40 years of age.

In certain instances, hyperuricemia is found in individuals with cardiovascular disease (CVD) and/or renal disease. In certain instances, hyperuricemia is found in individuals with prehypertension, hypertension, increased proximal sodium reabsorption, microalbuminuria, proteinuria, kidney disease, obesity, hypertriglyceridemia, low high-density lipoprotein cholesterol, hyperinsulinemia, hyperleptinemia, hypoadiponectinemia, peripheral, carotid and coronary artery disease, atherosclerosis, congestive heart failure, stroke, tumor lysis syndrome, endothelial dysfunction, oxidative stress, elevated renin levels, elevated endothelin levels, and/or elevated C-reactive protein levels. In certain instances, hyperuricemia is found in individuals with obesity (e.g., central obesity), high blood pressure, hyperlipidemia, and/or impaired fasting glucose. In certain instances, hyperuricemia is found in individuals with metabolic syndrome. In certain instances, gouty arthritis is indicative of an increased risk of acute myocardial infarction. In some embodiments, administration of a compound described herein to an individual are useful for decreasing the likelihood of a clinical event associated with a disease or condition linked to hyperuricemia, including, but not limited to, prehypertension, hypertension, increased proximal sodium reabsorption, microalbuminuria, proteinuria, kidney disease, obesity, hypertriglyceridemia, low high-density lipoprotein cholesterol, hyperinsulinemia, hyperleptinemia, hypoadiponectinemia, peripheral, carotid and coronary artery disease, atherosclerosis, congestive heart failure, stroke, tumor lysis syndrome, endothelial dysfunction, oxidative stress, elevated renin levels, elevated endothelin levels, and/or elevated C-reactive protein levels.

In some embodiments, a compound or compound form as described herein is administered to an individual suffering from a disease or condition requiring treatment with a diuretic. In some embodiments, a compound or compound form as described herein is administered to an individual suffering from a disease or condition requiring treatment with a diuretic, wherein the diuretic causes renal retention of urate. In some embodiments, the disease or condition is congestive heart failure or essential hypertension.

In some embodiments, administration of a compound or compound form as described herein to an individual is useful for improving motility or improving quality of life.

In some embodiments, administration of a compound or compound form as described herein to an individual is useful for treating or decreasing the side effects of cancer treatment.

In some embodiments, administration of a compound or compound form as described herein to an individual is useful for decreasing kidney toxicity of cis-platin.

In certain instances, gout is treated by lowering the production of uric acid. In certain instances, gout is treated by increasing the excretion of uric acid. In certain instances, gout is treated by a URAT 1 inhibitor, a xanthine oxidase inhibitor, a xanthine dehydrogenase inhibitor, a xanthine oxidoreductase inhibitor, a purine nucleoside phosphorylase (PNP) inhibitor, a uric acid transporter (URAT) inhibitor, a glucose transporter (GLUT) inhibitor, a GLUT-9 inhibitor, a solute carrier family 2 (facilitated glucose transporter), member 9 (SLC2A9) inhibitor, an organic anion transporter (OAT) inhibitor, an OAT-4 inhibitor, or combinations thereof. In general, the goals of gout treatment are to i) reduce the pain, swelling and duration of an acute attack, and ii) prevent future attacks and joint damage. In certain instances, gout attacks are treated successfully using a combination of treatments. In certain instances, gout is one of the most treatable forms of arthritis.

i) Treating the Gout Attack.

In certain instances, the pain and swelling associated with an acute attack of gout can be addressed with medications such as acetaminophen, steroids, nonsteroidal anti-inflammatory drugs (NSAIDs), adrenocorticotropic hormone (ACTH) or colchicine. In certain instances, proper medication controls gout within 12 to 24 hours and treatment is stopped after a few days. In certain instances, medication is used in conjunction with rest, increased fluid intake, ice-packs, elevation and/or protection of the affected area/s. In certain instances, the aforementioned treatments do not prevent recurrent attacks and they do not affect the underlying diseases of abnormal uric acid metabolism.

ii) Preventing Future Attacks.

In certain instances, reducing serum uric acid levels below the saturation level is the goal for preventing further gout attacks. In some cases, this is achieved by decreasing uric acid production (e.g. allopurinol), or increasing uric acid excretion with uricosuric agents (e.g. probenecid, sulfinpyrazone, benzbromarone).

In certain instances, allopurinol inhibits uric acid formation, resulting in a reduction in both the serum and urinary uric acid levels and becomes fully effective after 2 to 3 months.

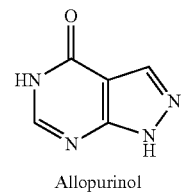
Allopurinol

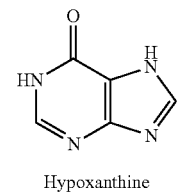
Hypoxanthine

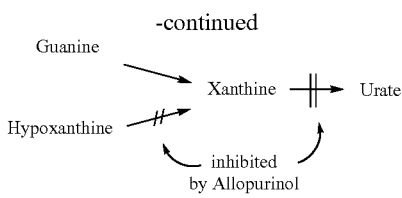

In certain instances, allopurinol is a structural analogue of hypoxanthine, (differing only in the transposition of the carbon and nitrogen atoms at positions 7 and 8), which inhibits the action of xanthine oxidase, the enzyme responsible for the conversion of hypoxanthine to xanthine, and xanthine to uric acid. In certain instances, it is metabolized to the corresponding xanthine analogue, alloxanthine (oxypurinol), which is also an inhibitor of xanthine oxidase. In certain instances, alloxanthine, though more potent in inhibiting xanthine oxidase, is less pharmaceutically acceptable due to low oral bioavailability. In certain instances, fatal reactions due to hypersensitivity, bone marrow suppression, hepatitis, and vasculitis have been reported with Allopurinol. In certain instances, the incidence of side effects may total 20% of all individuals treated with the drug. Treatment for diseases of uric acid metabolism has not evolved significantly in the following two decades since the introduction of allopurinol.

In certain instances, uricosuric agents (e.g., probenecid, sulfinpyrazone, and benzbromarone) increase uric acid excretion. In certain instances, probenecid causes an increase in uric acid secretion by the renal tubules and, when used chronically, mobilizes body stores of urate. In certain instances, 25-50% of individuals treated with probenecid fail to achieve reduction of serum uric acid levels <6 mg/dL. In certain instances, insensitivity to probenecid results from drug intolerance, concomitant salicylate ingestion, and renal impairment. In certain instances, one-third of the individuals develop intolerance to probenecid. In certain instances, administration of uricosuric agents also results in urinary calculus, gastrointestinal obstruction, jaundice and anemia.

Successful treatment aims to reduce both the pain associated with acute gout flare and long-term damage to the affected joints Therapeutic goals include providing rapid and safe pain relief, preventing further attacks, preventing the formation of tophi and subsequent arthritis, and avoiding exacerbating other medical conditions. Initiation of treatment depends upon the underlying causes of hyperuricemia, such as renal function, diet, and medications. While gout is a treatable condition, there are limited treatments available for managing acute and chronic gout and a number of adverse effects are associated with current therapies. Medication treatment of gout includes pain management, prevention or decrease in joint inflammation during an acute gouty attack, and chronic long-term therapy to maintain decreased serum uric acid levels.

Nonsteroidal anti-inflammatory drugs (NSAIDs) are effective anti-inflammatory medications for acute gout but are frequently associated with irritation of the gastrointestinal (GI) system, ulceration of the stomach and intestines, and occasionally intestinal bleeding. Colchicine for acute gout is most commonly administered orally as tablets (every 1-2 hours until there is significant improvement in pain or the patient develops GI side effects such as severe diarrhea, nausea and vomiting), or intravenously. Corticosteroids, given in short courses, can be administered orally or injected directly into the inflamed joint.

Medications are available for reducing blood uric acid levels that either increase renal excretion of uric acid by inhibiting re-uptake or reduce production of uric acid by blockade of xanthine oxidase. These medicines are generally not initiated until after the inflammation from acute gouty arthritis has subsided because they may intensify the attack. If they are already being taken prior to the attack, they are continued and only adjusted after the attack has resolved. Since many subjects with elevated blood uric acid levels may not develop gouty attacks or kidney stones, the decision for prolonged treatment with uric acid-lowering medications is individualized.

Kits

The compounds, compound forms, compositions and methods described herein provide kits for the treatment of diseases and disorders, such as the ones described herein. These kits comprise a compound, compound form, compounds, compound forms or compositions described herein in a container and, optionally, instructions teaching the use of the kit according to the various methods and approaches described herein. Such kits, in some embodiments, also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. Kits described herein are provided, marketed and/or promoted to health providers, including physicians, nurses, pharmacists, formulary officials, and the like. Kits are also, in some embodiments, marketed directly to the consumer.

Provided in certain embodiments, are compositions or kits comprising 2-(5-bromo-4-(4-cyclopropylnaphthalen-1-yl)-4H-1,2,4-triazol-3-ylthio)acetate (e.g., a polymorph thereof, such as Form 1), a double low density polyethylene plastic bag, and an HDPE container. In further embodiments, the composition or kit further comprises a foil bag (e.g., an anhydrous foil bag, such as a heat sealed anhydrous foil bag). In some embodiments, the composition or kit further comprises a desiccant; in still other embodiments, a desiccant is not necessary and/or present. In some instances, such packing improves the stability of the 2-(5-bromo-4-(4-cyclopropylnaphthalen-1-yl)-4H-1,2,4-triazol-3-ylthio)acetate (e.g., Form 1).

In some embodiments, the compounds, compound forms and pharmaceutical compositions described herein are utilized for diagnostics and as research reagents. For example, in some embodiments, the compounds, compound forms and pharmaceutical compositions, either alone or in combination with other compounds, are used as tools in differential and/or combinatorial analyses to elucidate expression patterns of genes expressed within cells and tissues. As one non-limiting example, expression patterns within cells or tissues treated with one or more compounds are compared to control cells or tissues not treated with compounds and the patterns produced are analyzed for differential levels of gene expression as they pertain, for example, to disease association, signaling pathway, cellular localization, expression level, size, structure or function of the genes examined. These analyses are performed on stimulated or unstimulated cells and in the presence or absence of other compounds which affect expression patterns.

Besides being useful for human treatment, the compounds, compound forms and pharmaceutical compositions described herein are also useful for veterinary treatment of animals.

The examples and preparations provided below further illustrate and exemplify the compounds of the present invention and methods of preparing such compounds. It is to be understood that the scope of the present invention is not limited in any way by the scope of the following examples and preparations.

EXAMPLES

I. Preparation of 2-(5-bromo-4-(4-cyclopropylnaphthalen-1-yl)-4H-1,2,4-triazol-3-ylthio)acetic acid

Example 1A

Preparation of 2-(5-bromo-4-(4-cyclopropylnaphthalen-1-yl)-4H-1,2,4-triazol-3-ylthio)acetic acid via methyl 2-(5-amino-4-(4-cyclopropylnaphthalen-1-yl)-4H-1,2,4-triazol-3-ylthio)acetate intermediate 2-(5-Bromo-4-(4-cyclopropylnaphthalen-1-yl)-4H-1,2,4-triazol-3-ylthio)acetic acid was prepared according to previously described procedures (see US patent application publication US 2009/0197825) as outlined in the scheme below.

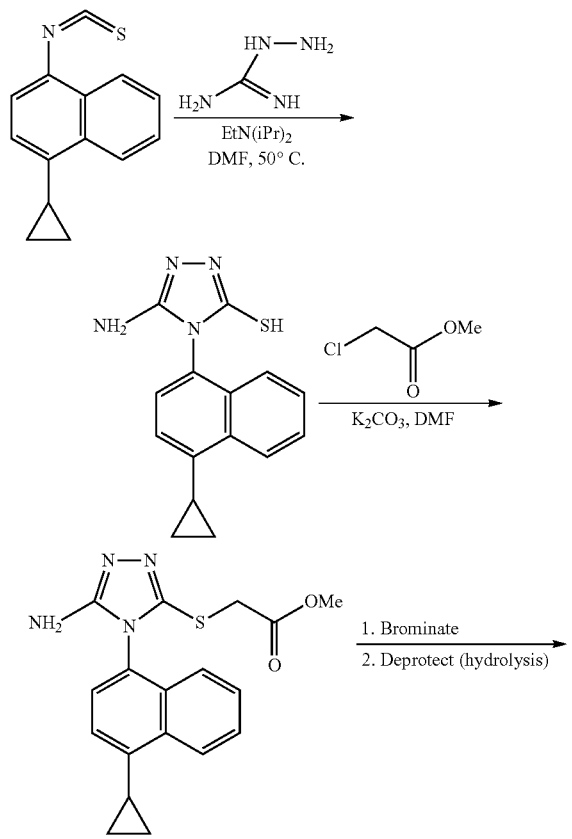

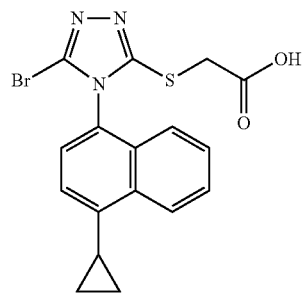 [SMILES: O=C(O)CSc1nnc(Br)n1-c1ccc(C2CC2)c2ccccc12]

Example 1B

Preparation of 2-(5-bromo-4-(4-cyclopropylnaphthalen-1-yl)-4H-1,2,4-triazol-3-ylthio)acetic acid via 2-(4-(4-cyclopropylnaphthalen-1-yl)-5-hydroxy-4H-1,2,4-triazol-3-ylthio)acetic acid intermediate

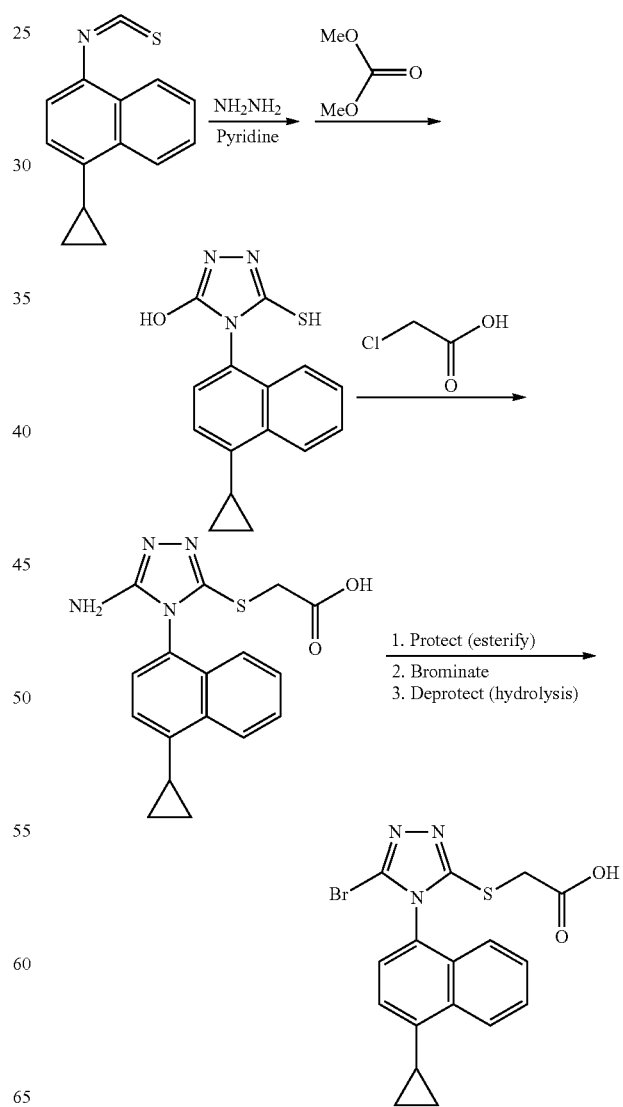

Preparation of 1-cyclopropyl-4-isothiocyanatonaphthalene has been previously described (see US patent application publication US 2009/0197825). In brief, 1-bromonaphthalene is coupled with cyclopropylmagnesium bromide to form 1-cyclopropylnaphthalene. Reaction with sodium nitrite forms the nitro derivative which is reduced by treatment with hydrogen over Pd/C to form 1-amino-4-cyclopropylnaphthalene. Finally, reaction with thiophosgene provides 1-cyclopropyl-4-isothiocyanatonaphthalene.

1-Cyclopropyl-4-isothiocyanatonaphthalene is reacted with hydrazine and then cyclized in the presence of dimethyl carbonate to form 4-(4-cyclopropylnaphthalen-1-yl)-5-mercapto-4H-1,2,4-triazol-3-ol.

Coupling of 4-(4-cyclopropylnaphthalen-1-yl)-5-mercapto-4H-1,2,4-triazol-3-ol with 2-chloroacetic acid provides 2-(4-(4-cyclopropylnaphthalen-1-yl)-5-hydroxy-4H-1,2,4-triazol-3-ylthio)acetic acid.

Bromination of 2-(4-(4-cyclopropylnaphthalen-1-yl)-5-hydroxy-4H-1,2,4-triazol-3-ylthio)acetic acid, utilizing protecting groups as required (such as protecting the acid as the i-propyl ester), provides 2-(5-bromo-4-(4-cyclopropylnaphthalen-1-yl)-4H-1,2,4-triazol-3-ylthio)acetic acid.

Example 1C

Preparation of sodium 2-(5-bromo-4-(4-cyclopropylnaphthalen-1-yl)-4H-1,2,4-triazol-3-ylthio)acetate from methyl 2-(5-bromo-4-(4-cyclopropylnaphthalen-1-yl)-4H-1,2,4-triazol-3-ylthio)acetate

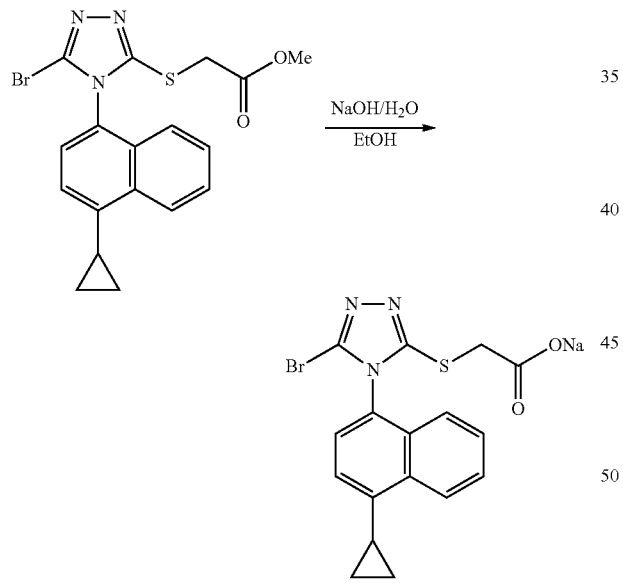

Aqueous sodium hydroxide solution (1N, 3.0 L, 3.0 mol, 1.25 eq) was added to a cooled (15-18° C.) mixture of methyl 2-(5-bromo-4-(4-cyclopropylnaphthalen-1-yl)-4H-1,2,4-triazol-3-ylthio)acetate-form 2 (1.0 kg, 2.39 mol, 1 eq) and ethanol (9 L), at a rate to maintain an internal temperature <25° C. The mixture was then stirred at 20-25° C. (maintaining pH≥12), while monitoring by HPLC and considered complete when the sum of methyl and ethyl esters <0.5%, (~3 hours). The mixture was filtered through a medium frit funnel (10-16 micron) and the filtrate concentrated in vacuo (40° C.) to a final volume of 5.2 L. Water (0.6 L) was added and the solution cooled to 0-5° C. with stirring. The resulting slurry was warmed (17-18° C.) over 1 h, then cooled (0-5° C.) over 2-3 h, and held at 0-5° C. for an additional 6-9 h. The slurry was then filtered through a jacketed filter funnel (0-5° C.) lined with filter paper (3 micron) or filter cloth. The resulting cake was washed with pre-chilled (3-5° C.) water (3×1.25 L), allowed to de-liquor on the funnel (at least 3 h), and further dried in a vacuum oven (18-25° C., nitrogen sweep) until water content <13% w/w (~8 days). Sodium 2-(5-amino-4-(4-cyclopropylnaphthalen-1-yl)-4H-1,2,4-triazol-3-ylthio)acetate was isolated as a light yellow solid (696.4 g; KF=13%).

II. Preparation of Crystalline Polymorph Forms of 2-(5-bromo-4-(4-cyclopropylnaphthalen-1-yl)-4H-1,2,4-triazol-3-ylthio)acetic acid Example 2

Preparation of 2-(5-bromo-4-(4-cyclopropylnaphthalen-1-yl)-4H-1,2,4-triazol-3-ylthio)acetic acid-form 1

2-(5-Bromo-4-(4-cyclopropylnaphthalen-1-yl)-4H-1,2,4-triazol-3-ylthio)acetic acid-form 1 is prepared from crude sodium 2-(5-bromo-4-(4-cyclopropylnaphthalen-1-yl)-4H-1,2,4-triazol-3-ylthio)acetate as described below:

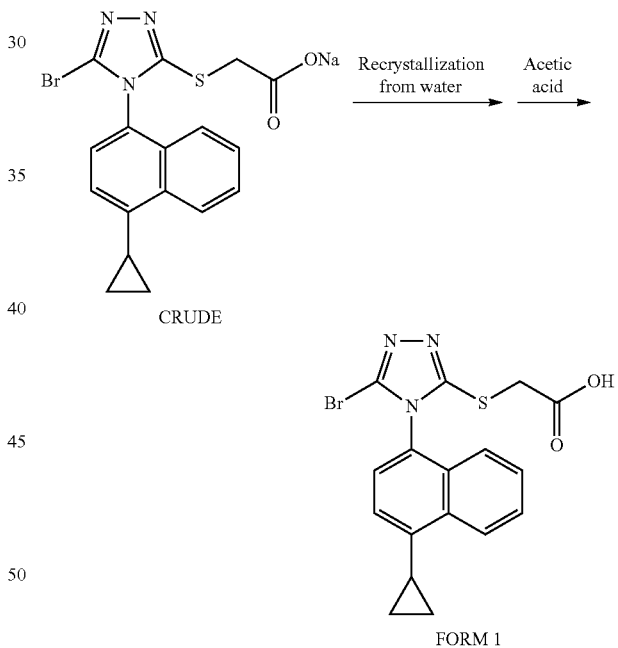

Step 1:

Sodium 2-(5-bromo-4-(4-cyclopropylnaphthalen-1-yl)-4H-1,2,4-triazol-3-ylthio)acetate (60 g) and water (300 mL) were stirred and briefly heated (40-50° C.) until all solids dissolved. The solution was cooled and stirred in an ice bath for 1-2 hrs, after which time crystals began to form (or if crystallization had not begun, the solution was seeded with a small amount of sodium 2-(5-bromo-4-(4-cyclopropylnaphthalen-1-yl)-4H-1,2,4-triazol-3-ylthio)acetate crystals). Stirring in the ice bath was continued until crystallization was complete, and then the solid isolated by filtration through a sintered filter funnel (medium porosity) under vacuum. The filter cake was washed with ice-cold water (sufficient to cover the filter cake) and the liquid completely drained under vacuum to provide wet filter cake (126.5 g).

Step 2:

The filter cake was dissolved in water (~70 g present in the filter cake plus 130 mL; concentration 200-250 mg/mL) at 60-70° C., and slowly added to acetic acid (200 mL). The acetic acid/water (1:1 v/v) solution was cooled to room temperature under continuous stirring, and then further cooled to 0° C., resulting in the formation of crystals which were isolated by vacuum filtration over a medium porosity sintered filter funnel. The solids were washed with ice-cold acid/water (1:1 v/v) and dried in a vacuum oven to provide 2-(5-bromo-4-(4-cyclopropylnaphthalen-1-yl)-4H-1,2,4-triazol-3-ylthio)acetic acid (39.5 g, 78%).

Example 3

Preparation of 2-(5-bromo-4-(4-cyclopropylnaphthalen-1-yl)-4H-1,2,4-triazol-3-ylthio)acetic acid-form 2

2-(5-Bromo-4-(4-cyclopropylnaphthalen-1-yl)-4H-1,2,4-triazol-3-ylthio)acetic acid-form 2 is prepared from sodium 2-(5-bromo-4-(4-cyclopropylnaphthalen-1-yl)-4H-1,2,4-triazol-3-ylthio)acetate as described below:

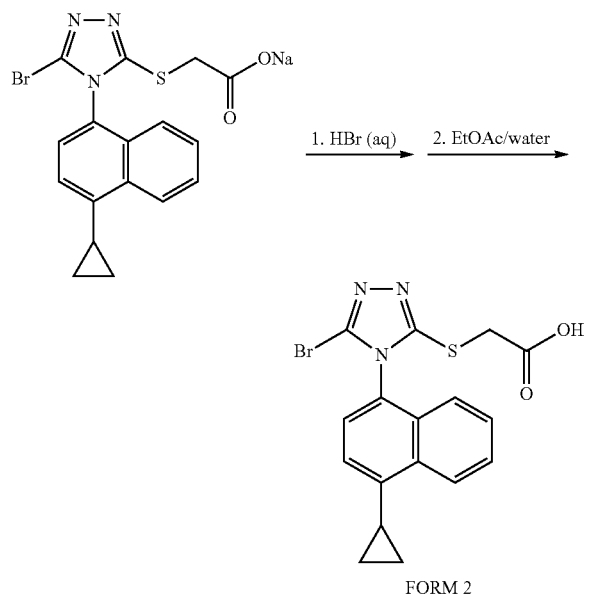

FORM 2

A suspension of sodium 2-(5-bromo-4-(4-cyclopropylnaphthalen-1-yl)-4H-1,2,4-triazol-3-ylthio)acetate (50.0 g of crude sample 97.6% a/a; KF=12.6%; 43.3 g calculated actual) and deionized water (217 mL) was heated (30-35° C.) with vigorous stirring for 10-15 min, during which time the slurry dissolved leaving only trace solids. The mixture was filtered through a medium-frit filter funnel and the clear filtrate cooled to 10° C. Approximately one half of a mixture of aqueous hydrogen bromide solution (48 wt %, 18 g, 106.8 mmol, 1.05 eq) and deionized water (~13 mL) was added to the filtrate over 10 min, at 10-15° C., during which time some solids were formed. Ethyl acetate (347 mL) was added with vigorous stirring resulting in dissolution of all solids. The remaining hydrogen bromide solution was added over 10 min at 10° C., and stirring continued for 5-10 min, during which time a cloudy suspension formed. Stirring was stopped, the phases allowed to separate and the aqueous layer removed. The organic layer was washed with deionized water (110 mL) with vigorous stirring for 5-10 min, and after phase separation the aqueous layer removed. The organic layer was heated to 45-50° C. and solvents removed using gentle vacuum, resulting in the formation of a slurry (final volume ~200 mL), which was warmed (45-50° C.) with moderate stirring for 1 h, gradually (3-4 h) cooled to 20-25° C., and held at 20-25° C. for an additional 12 h, and finally cooled to 5-10° C. and held for 20-30 min. The slurry was then filtered under vacuum through a Buchner funnel lined with Whatman No. 3 filter paper. There were fast filtering solids and the mother liquor was cycled through the vessel to recover residual solids which were collected with the initial batch. The solids were washed with cold (5° C.) ethyl acetate (26 mL) and allowed to dry on the funnel for at least 10 min, then soaked in n-heptane (30 mL) for at least 10 min and the vacuum reapplied for ~6 h. The solids were transferred to a drying dish and dried in a vacuum oven (25 mmHg) for at least 16 h at 35-40° C., with nitrogen sweep. 2-(5-Bromo-4-(4-cyclopropylnaphthalen-1-yl)-4H-1,2,4-triazol-3-ylthio)acetic acid-form 2 was obtained as a free flowing off-white solid (28.39 g, 69%), containing trace amounts of water (0.16 wt %) and ethyl acetate (700 ppm).

| Materials | Amount |
| --- | --- |
| Sodium 2-(5-bromo-4-(4-cyclopropyl naphthalen-1-yl)-4H-1,2,4-triazol-3-ylthio)acetate | 50.0 g crude (43.3 g corrected) |
| Hydrogen bromide (48 wt %) | 18.0 g |
| Water | 217 mL |
| Ethyl acetate | 346.7 mL |
| Water (wash 1) | 108.3 mL |
| Water (wash 2) | 108.3 mL |
| Ethyl acetate (wash) | 26 mL |
| n-Heptane (wash) | 30 mL |

Example 4

Conversion of 2-(5-bromo-4-(4-cyclopropylnaphthalen-1-yl)-4H-1,2,4-triazol-3-ylthio)acetic acid-Polymorph Form 1 to Polymorph Form 2

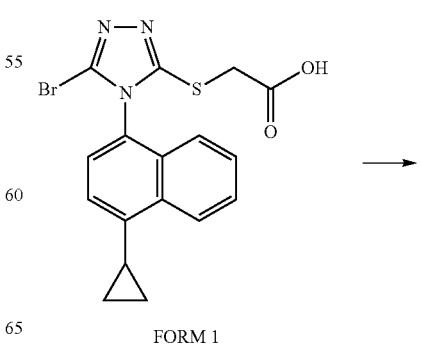

FORM 1

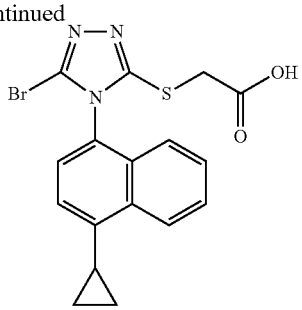

FORM 2

Method 1

Ethyl acetate (200 mL) was added to a solution of 2-(5-bromo-4-(4-cyclopropylnaphthalen-1-yl)-4H-1,2,4-triazol-3-ylthio)acetic acid-polymorph form 1 (30 g) in acetone (200 mL) at 60° C. A portion of the solvent (~200 mL) was removed under low vacuum and fresh ethyl acetate (200 mL) was added, followed by another distillation cycle, during which crystallization began. The temperature of the water bath was slowly increased to 70° C., during which time four additional ethyl acetate addition/distillation cycles were carried out to a final volume of ~200 mL. The mixture was allowed to cool slowly to room temperature and then placed in the fridge overnight. Solids were isolated by filtration, washed with ice-cold ethyl acetate and dried in a vacuum oven to provide of 2-(5-bromo-4-(4-cyclopropylnaphthalen-1-yl)-4H-1,2,4-triazol-3-ylthio)acetic acid-form 2.

Method 2

A solution of 2-(5-bromo-4-(4-cyclopropylnaphthalen-1-yl)-4H-1,2,4-triazol-3-ylthio)acetic acid-form 1 in one of the solvents listed below was slowly evaporated at room temperature to crystallize, refrigerated, the solid crystals isolated and washed with solvent to produce Solid Polymorph form 2, containing trace amounts of solvent and water, as indicated.

| Solvent | Solvent content (%) | Water content (%) | Purity | Polymorph Form |
|---|---|---|---|---|
| Butan-2-one | 0.35 | 0.36 | | 2 |
| | 0.49 | 0.53 | | |
| tert-Butanol | 0.32 | 0.17 | 94% | 2 |
| | 0.72 | 0.5 | 4% impurities | |
| Dichloromethane | 0.3 | 0.5 | | 2 |

Method 3

Solid Polymorph form 1 was held in equilibrium with its saturated acetonitrile, ethyl acetate or toluene solution at 60° C. for 6 days to produce Solid Polymorph form 2.

Solid Polymorph form 1 held in equilibrium with its saturated acetone solution at 60° C. for 6 days resulted in decomposition.

Method 4

Solid Polymorph form 1 and solvent (20 µL) were heated at 60° C. for 13 days to produce Solid Polymorph form 2.

| form 1 (mg) | Solvent | Polymorph Form Isolated |
|---|---|---|
| 928 | DMF | 2 |
| 927 | Dioxane | 2 |
| 883 | Acetic acid | 2 |
| 844 | Toluene | 2 |
| 844 | Acetonitrile/toluene (20 µL each) | 2 |
| 844 | Acetonitrile | 1 & 2 |
| 867 | iso-Propanol | 1 & 2 |
| 944 | Water | 1 |

III. Analysis of Crystalline Polymorph Forms of 2-(5-bromo-4-(4-cyclopropylnaphthalen-1-yl)-4H-1,2,4-triazol-3-ylthio)acetic acid Example 5A Analysis of Crystalline Polymorph Form 1

X-Ray Powder Diffraction

The X-ray powder diffraction pattern of polymorph form 1 is shown in FIGS. 1 (raw data) and 2 (background subtracted and Kα2 stripped); observed and representative peaks in the XRPD pattern are shown in the tables below (generated on background corrected and Kα2 stripped file).

| form 1 Observed | | |
|---|---|---|
| °2θ | d space (Å) | Intensity (%) |
| 10.32 | 8.562 | 100 |
| 18.84 | 4.706 | 32.7 |
| 20.75 | 4.277 | 23.2 |
| 27.28 | 3.266 | 13.6 |
| 27.60 | 3.229 | 11 |
| 21.54 | 4.123 | 10.4 |
| 25.53 | 3.487 | 9.8 |
| 6.80 | 12.989 | 9.4 |
| 24.97 | 3.563 | 9.1 |
| 28.43 | 3.137 | 8.4 |
| 19.98 | 4.441 | 6.9 |
| 29.35 | 3.040 | 6.7 |
| 15.88 | 5.577 | 5.4 |
| 23.13 | 3.842 | 4.8 |
| 26.34 | 3.381 | 4.8 |
| 18.56 | 4.777 | 4.1 |

| form 1 Representative | | |
|---|---|---|
| °2θ | d space (Å) | Intensity (%) |
| 10.32 | 8.562 | 100 |
| 18.84 | 4.706 | 32.7 |
| 20.75 | 4.277 | 23.2 |
| 27.28 | 3.266 | 13.6 |

Differential Scanning Calorimetry (DSC)

The differential scanning calorimetry trace for form 1 is shown in FIG. 3; a transition temperature of 150.7° C. was recorded.

Scanning Electron Microscopy (SEM)

SEM analysis showed form 1 primary crystals are composed of agglomerates (typical size ~25 µm) of plate-like crystals (size ~5 µm).

Thermogravimetric Analysis (TGA)

Figure 4:
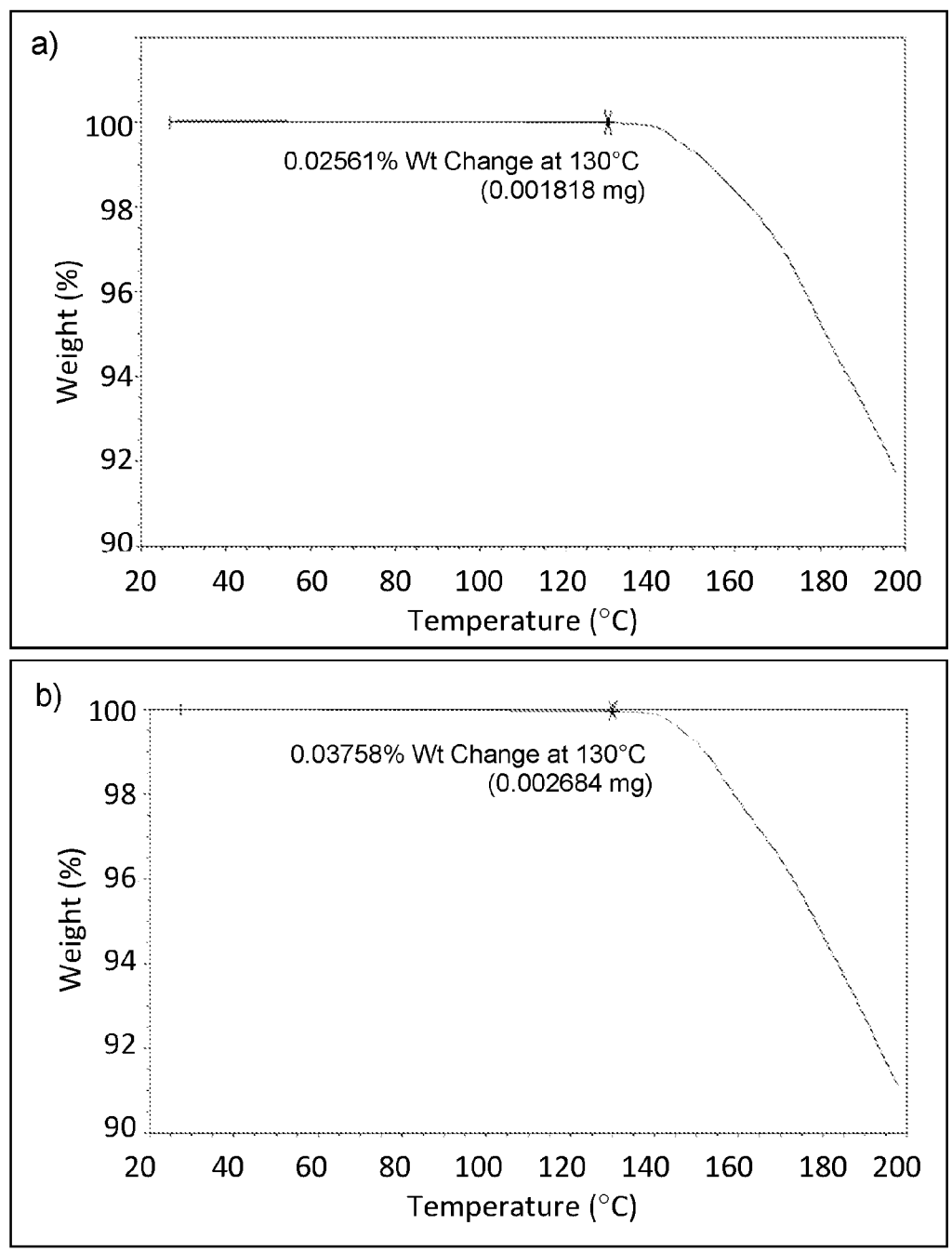
FIG. 4 represents illustrative Thermogravimetric Analyses (a) Rep 1 and (b) Rep 2 of Polymorph form 1.

Replicate TGA scans for form 1 are shown in FIGS. 4 (*a*) and (*b*), indicating the material does not contain significant levels of volatiles Solubility Form 1 (~25 mg) and acetate buffer (25 mM, pH 5, 4 mL), prepared with and without sodium chloride (ionic strength adjusted to=0.1M), were placed in a glass vial which was sealed and placed on a laboratory rotator in a 25° C. incubator. After 1, 5, and 7 days the samples were filtered and assayed by HPLC. Form 1 solubility (mg/mL), at the various time points, with and without sodium chloride, is shown in the table below:

|  | Day 1 | Day 5 | Day 7 |
| --- | --- | --- | --- |
| No NaCl | 0.2652 (pH 4.95) | 0.2134 (pH 4.85) | 0.1569 (pH 4.75) |
| NaCl (I = 0.1) | 0.2995 | 0.2566 (pH 4.79) | 0.3045 (pH 4.81) |

Example 5B

Analysis of Crystalline Polymorph Form 2

X-Ray Powder Diffraction

The X-ray powder diffraction pattern of polymorph form 2 is shown in FIGS. 5 (raw data) and 6 (background subtracted and Kα2 stripped); observed and representative peaks in the XRPD pattern are shown in the tables below (generated on background corrected and Kα2 stripped file).

| form 2 Observed | | |
| --- | --- | --- |
| °2θ | d space (Å) | Intensity (%) |
| 7.97 | 11.086 | 13.8 |
| 9.66 | 9.148 | 26.1 |
| 10.46 | 8.449 | 83.8 |
| 11.96 | 7.394 | 41.3 |
| 12.55 | 7.046 | 16.7 |
| 12.94 | 6.836 | 15.7 |
| 13.82 | 6.402 | 41.6 |
| 16.19 | 5.471 | 49.8 |
| 18.21 | 4.867 | 74.0 |
| 18.76 | 4.727 | 81.4 |
| 19.02 | 4.662 | 35.6 |
| 19.51 | 4.548 | 15.9 |
| 19.83 | 4.474 | 100.0 |
| 20.40 | 4.349 | 13.4 |
| 21.36 | 4.157 | 12.3 |
| 22.50 | 3.948 | 36.7 |
| 22.88 | 3.884 | 30.6 |
| 23.08 | 3.850 | 56.1 |
| 24.01 | 3.704 | 42.1 |
| 25.15 | 3.539 | 35.2 |
| 25.46 | 3.496 | 20.5 |
| 26.06 | 3.417 | 13.4 |
| 26.51 | 3.360 | 35.7 |
| 27.97 | 3.187 | 26.8 |
| 29.93 | 2.983 | 37.0 |
| 30.42 | 2.936 | 12.4 |
| 31.77 | 2.814 | 17.1 |
| 32.35 | 2.765 | 38.2 |
| 34.26 | 2.615 | 12.8 |
| 38.01 | 2.366 | 16.5 |
| 38.88 | 2.314 | 10.0 |

| form 2 Representative | | |
| --- | --- | --- |
| °2θ | d space (Å) | Intensity (%) |
| 19.83 | 4.474 | 100.0 |
| 10.46 | 8.449 | 83.8 |
| 18.76 | 4.727 | 81.4 |
| 18.21 | 4.867 | 74.0 |
| 23.08 | 3.850 | 56.1 |

Figure 7:
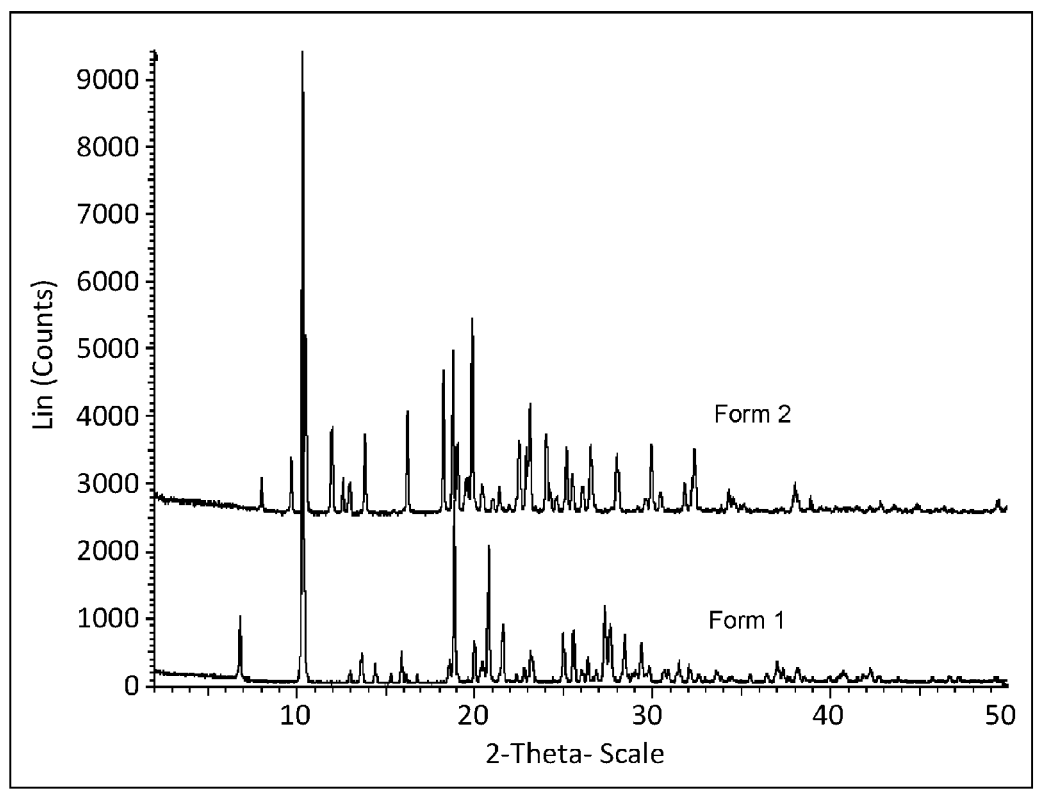
FIG. 7 represents an illustrative overlay of X-ray Powder Diffraction Patterns of Polymorph form 1 (lower) and form 2 (upper).

FIG. 7, shows an overlay of the XRPD Patterns (y-axis offset) of form 1 (lower) and form 2 (upper).

Differential Scanning Calorimetry (DSC)

The differential scanning calorimetry trace for form 2 is shown in FIG. 8, a melting point at 174.7° C. was recorded.

$^1$H NMR Spectroscopy

Figure 9:
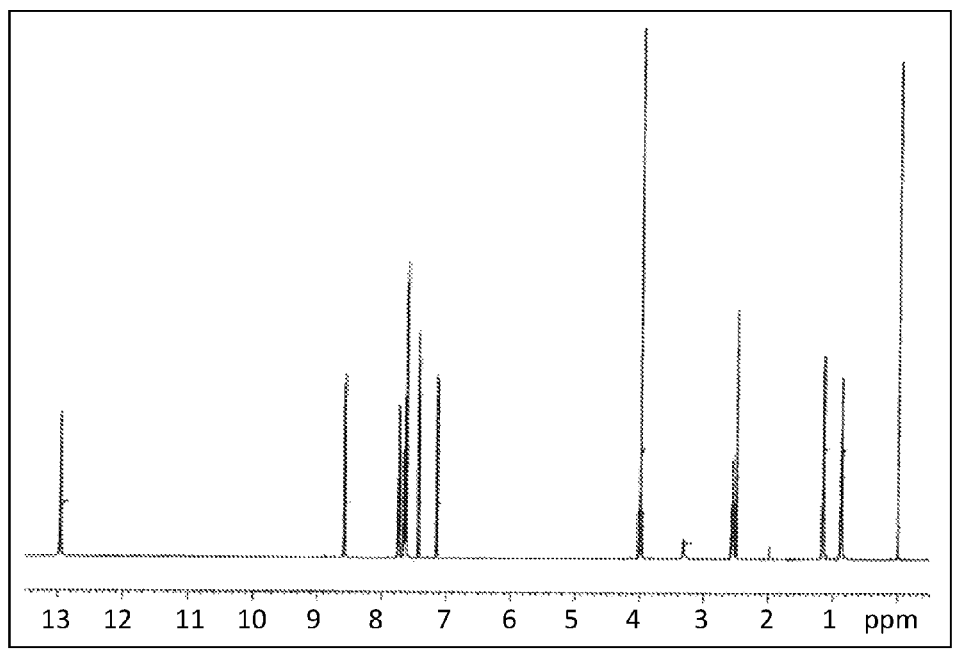
FIG. 9 represents an illustrative $^1$H NMR (DMSO-$d_6$) spectrum of Polymorph form 2.

The $^1$H NMR spectrum, taken in DMSO-d$_6$, of polymorph form 2 is shown in FIG. 9 and the major peaks listed in the table below:

| ppm | peak | integration |
| --- | --- | --- |
| 12.96 | s | 1.00 |
| 8.58 | d | 1.01 |
| 7.74 | td | 1.01 |
| 7.65 | m | 2.02 |
| 7.44 | d | 1.01 |
| 7.16 | d | 1.00 |
| 3.99 | d | 2.02 |
| 2.49-2.58 | m | 1.00 |
| 1.16 | m | 2.03 |
| 0.88 | d | 2.01 |

HPLC

Figure 10:
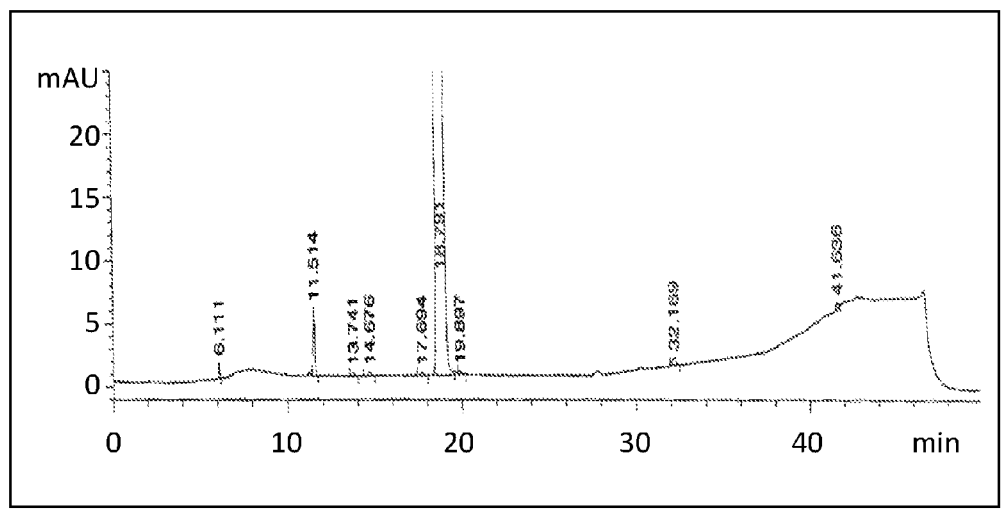
FIG. 10 represents an illustrative HPLC trace of Polymorph form 2.

The HPLC trace of polymorph form 2 is shown in FIG. 10. The peak listing for the trace is given in the table below:

| Peak # | Ret time (min) | Type | Width (min) | Area (mAU * s) | Area (%) |
| --- | --- | --- | --- | --- | --- |
| 1 | 6.111 | BB | 0.0621 | 5.24158 | 0.0438 |
| 2 | 11.514 | VB | 0.1157 | 39.57644 | 0.3311 |
| 3 | 13.741 | BB | 0.1436 | 2.56681 | 0.0215 |
| 4 | 143676 | BB | 0.1463 | 3.02621 | 0.0253 |
| 5 | 17.694 | BB | 0.1785 | 3.37245 | 0.0282 |
| 6 | 18.791 | BB | 0.2269 | 11,881.6 | 99.3931 |
| 7 | 19.891 | BB | 0.2502 | 5.15241 | 0.0431 |
| 8 | 32.169 | BB | 0.1785 | 8.54182 | 0.0715 |
| 9 | 41.636 | BB | 0.1163 | 5.06670 | 0.0424 |

Scanning Electron Microscopy (SEM)

SEM analysis showed form 2 primary crystals are composed of agglomerates (typical size ~25 μm) of column-like crystals (size ~10 μm).

Thermogravimetric Analysis (TGA)

Figure 11:
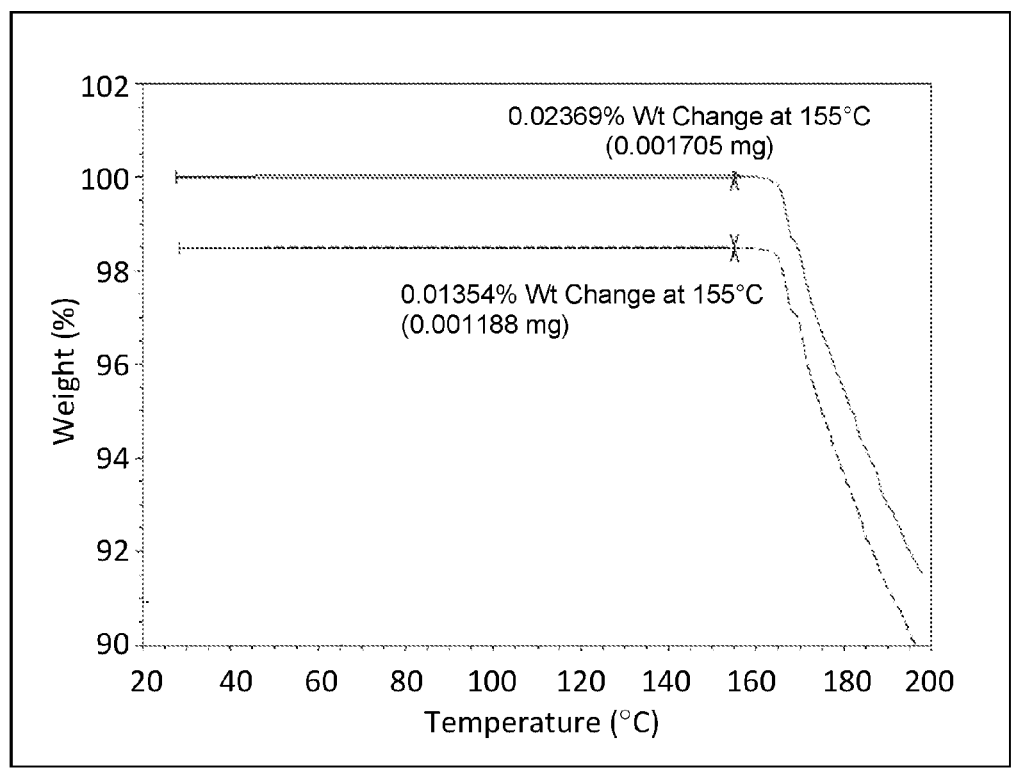
FIG. 11 represents an illustrative Thermogravimetric Analysis trace of Polymorph form 2.

Overlay of TGA scans for form 2 are shown in FIG. 11, indicating the material does not contain significant levels of volatiles.

Solubility

Form 2 (~25 mg) and acetate buffer (25 mM, pH 5, 4 mL), prepared with and without sodium chloride (ionic strength adjusted to=0.1M), were placed in a glass vial which was sealed and placed on a laboratory rotator in a 25° C. incubator. After 1, 5, and 7 days the samples were filtered and assayed by HPLC. Form 2 solubility (mg/mL), at the various time points, with and without sodium chloride, is shown in the table below:

|  | Day 1 | Day 5 | Day 7 |
| --- | --- | --- | --- |
| No NaCl | 0.1867 (pH 4.91) | 0.1957 (pH 4.73) | 0.1337 (pH 4.79) |
| NaCl (I = 0.1) | 0.2192 | 0.2441 (pH 4.83) | 0.2157 (pH 4.85) |

Form 2 of 2-(5-bromo-4-(4-cyclopropylnaphthalen-1-yl)-4H-1,2,4-triazol-3-ylthio)acetate was tested under various conditions to determine drug substance stability. No degradation of packaged Form 2 was observed for 1 month under accelerated conditions (40° C.-75% RH, or 25° C.-60% RH). Packaging was in a double low density polyethylene plastic bags inside a HDPE container.

Stability of Crystalline Polymorph 2-(5-bromo-4-(4-cyclopropylnaphthalen-1-yl)-4H-1,2,4-triazol-3-ylthio)acetate The crystalline polymorphs of 2-(5-bromo-4-(4-cyclopropylnaphthalen-1-yl)-4H-1,2,4-triazol-3-ylthio)acetate were found to exhibit increased stability in comparison to the amorphous solid state form of the carboxylic acid. The improved stability of the crystalline polymorphs of 2-(5-bromo-4-(4-cyclopropylnaphthalen-1-yl)-4H-1,2,4-triazol-3-ylthio)acetate provides for the preparation of pharmaceutical dosage forms displaying reduced variability in the dosage present in a given dosage form, reduction in the presence of impurities in the final pharmaceutical product, and an improved shelf life of formulated dosage forms when compared to the pharmaceutical dosage form prepared with the amorphous solid state form of the carboxylic acid.

IV Analytical Techniques

Example 6A

X-Ray Powder Diffraction (XRPD)

XRPD patterns were collected on a Bruker D8 Advance diffractometer in the Bragg-Brentano theta/theta configuration. An incident x-ray beam was produced using a CuKα (λ=1.5418 Å) anode (tube voltage=40 kV, current=40 mA), made parallel with a 1.0 mm primary Soller slit on the source side and 1.0 mm secondary Soller slit on the detector side. CuKβ radiation was removed with a graphite monochromator slit of 1.0 mm on the detector side. A scintillation detector (NaI) was used with slit of 0.1 mm. A continuous scan of 0.02°2θ step size and 5 s per step from 2-50°2θ was used. Approximately 25 mg of material was carefully pressed onto a Si zero background wafer to ensure a flat preparation. Data were collected using Bruker Diffrac$^{plus}$ XRD Commander v2.3 software. Peak lists were generated using Bruker Diffrac$^{plus}$ EVA v9.0 software with background subtraction and Kα2 stripping. The instrument alignment check was done with a NIST alumina standard SRM1976. XRPD (Bruker D8 Advance) instrument conditions are summarized in the table below:

| Instrument Parameter | Setting |
| --- | --- |
| Configuration | Bragg-Brentano Theta/theta |
| Detector Type | Scintillation (NaI) |
| Source Type | CuKα = 1.5418 Å |
| Source Primary Soller Slit | 1.0 mm |
| Detector Secondary Soller Slit | 1.0 mm |
| Detector Slit | 0.1 mm |
| Monochromator (graphite) Slit | 1.0 mm |
| Scan Range | 2 to 50 °2θ |
| Step Size | 0.02 °2θ |
| Time per Step | 5 sec |

Example 6B

Differential Scanning Calorimetry (DSC)

Differential scanning calorimetry was performed using a TA Instruments Q2000 differential scanning calorimeter. Temperature calibration was performed using NIST traceable indium metal. Duplicate samples were prepared by sealing approximately 2-5 mg (accurately recorded) of material into a TA Tzero non-hermetic pan. A Tzero non-hermetic pan/lid was weighed and used on the reference side of the cell. Samples were heated at a rate of 10° C./min from 25° C. to 200° C., using a 50 mL/min nitrogen purge gas flow rate. The melting temperature ($T_m$) and the heat of melting ($\Delta H_m$) were measured using TA Universal Analysis software v4.4.

Example 6C

Scanning Electron Microscopy (SEM)

SEM images were collected on a JEOL SEM model JSM-6100. The sample was sprinkled onto an SEM stub containing double-sided carbon tape and was sputter coated with gold for 60 s using the Denton Desk II unit. The SEM was operated at 15 kV accelerating voltage. Images were collected using software DIPS v2.5 (Digital Imaging Processing System) with the slow scan set to 800×640 pixels and integrator at 50 μs with no averaging. Images were collected at magnification ranging from 50× to 5000×.

Example 6D

Thermogravimetric Analysis (TGA

Thermogravimetric analysis (TGA) was performed using a TA Instrument Q5000. Weight calibration was checked using a certified 50 mg weight. Duplicate samples were prepared by weighing ~5-10 mg material into a TA Pt pan. Samples were heated at a rate of 10° C./min to 200° C., using a 25 mL/min nitrogen purge gas flow rate. Weight losses were measured using TA Universal Analysis software v4.4.

What is claimed is:

1. A method for treating hyperuricemia associated with gout, comprising administering an effective amount of a crystalline polymorph of 2-(5-bromo-4-(4-cyclopropylnaphthalen-1-yl)-4H-1,2,4-triazol-3-ylthio)acetic acid:

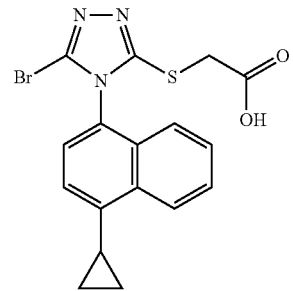 [SMILES: O=C(O)CSc1nnc(Br)n1-c1ccc(C2CC2)c2ccccc12]

characterized by peaks at 10.46, 18.76, and 19.83 °2θ±0.1°2θ.

2. The method of claim 1, wherein the crystalline polymorph is further characterized by at least one further peak at 18.21 or 23.08 °2θ±0.1°2θ.

3. The method of claim 1, wherein the crystalline polymorph exhibits an x-ray powder diffraction pattern substantially the same as the x-ray powder diffraction pattern shown in FIG. 5.

4. The method of claim 1, wherein the crystalline polymorph is prepared by a method comprising the step of crystallizing 2-(5-bromo-4-(4-cyclopropylnaphthalen-1-yl)-4H-1,2,4-triazol-3-ylthio)acetic acid from a mixture of water and ethyl acetate.

5. The method of claim 1, further comprising administering allopurinol.

6. The method of claim 1, further comprising administering febuxostat.

7. A method of treating hyperuricemia associated with gout, comprising administering an effective amount of a crystalline polymorph of 2-(5-bromo-4-(4-cyclopropylnaphthalen-1-yl)-4H-1,2,4-triazol-3-ylthio)acetic acid:

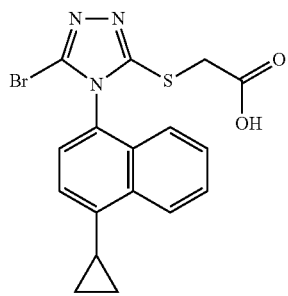 [SMILES: O=C(O)CSc1nnc(Br)n1-c1ccc(C2CC2)c2ccccc12]

characterized by peaks at 10.32, 18.84, and 20.75 °2θ±0.1°2θ.

8. The method of claim 7, wherein the crystalline polymorph is further characterized by at least two further peaks at 6.80, 21.54, 24.97, 25.53, 27.28 or 27.60 °2θ±0.1°2θ.

9. The method of claim 7, wherein the crystalline polymorph exhibits an x-ray powder diffraction pattern substantially the same as the x-ray powder diffraction pattern shown in FIG. 1.

10. The method of claim 7, wherein the crystalline polymorphic form of 2-(5-bromo-4-(4-cyclopropylnaphthalen-1-yl)-4H-1,2,4-triazol-3-ylthio)acetic acid is prepared by a method comprising the step of crystallizing 2-(5-bromo-4-(4-cyclopropylnaphthalen-1-yl)-4H-1,2,4-triazol-3-ylthio) acetic acid from a mixture of water and acetic acid.

11. The method of claim 7, further comprising administering allopurinol.

12. The method of claim 7, further comprising administering febuxostat.

* * * * *